(12) United States Patent
Anderson et al.

(10) Patent No.: US 9,861,277 B2
(45) Date of Patent: Jan. 9, 2018

(54) WAVEFRONT ANALYSER

(71) Applicant: Cylite Pty Ltd, Clayton (AU)

(72) Inventors: Trevor Bruce Anderson, Clayton (AU); Steven James Frisken, Vaucluse (AU); Grant Andrew Frisken, Mitcham (AU); Armin Georg Segref, Clayton (AU)

( * ) Notice: Subject to any disclaimer, the term of this patent is extended or adjusted under 35 U.S.C. 154(b) by 2 days.

(21) Appl. No.: 14/899,563

(22) PCT Filed: Jun. 20, 2014

(86) PCT No.: PCT/AU2014/000638
§ 371 (c)(1),
(2) Date: Dec. 18, 2015

(87) PCT Pub. No.: WO2014/201504
PCT Pub. Date: Dec. 24, 2014

(65) Prior Publication Data
US 2016/0135680 A1 May 19, 2016

(30) Foreign Application Priority Data

Jun. 20, 2013 (AU) ................................. 2013902254

(51) Int. Cl.
*A61B 3/14* (2006.01)
*A61B 3/00* (2006.01)
(Continued)

(52) U.S. Cl.
CPC .......... *A61B 3/1015* (2013.01); *A61B 3/0025* (2013.01); *A61B 3/107* (2013.01);
(Continued)

(58) Field of Classification Search
USPC .................................................. 351/206, 246
See application file for complete search history.

(56) References Cited

U.S. PATENT DOCUMENTS 7,230,717 B2 6/2007 Brock
7,982,881 B2 7/2011 Fercher
(Continued)

FOREIGN PATENT DOCUMENTS

CN 102589440 A 7/2012
WO 2013140396 A1 9/2013

OTHER PUBLICATIONS

Jaeken et al 'Fast scanning peripheral wave-front sensor for the human eye' Opt Exp 19 (2011) 7903-7913.
(Continued)

*Primary Examiner* — Jack Dinh
(74) *Attorney, Agent, or Firm* — Darren Gardner

(57) ABSTRACT

Interferometry-based methods and apparatus are presented for analyzing one or more wavefronts from a sample, in which the sample wavefronts are interfered with two or more reference wavefronts to produce two or more interferograms in a sufficiently short time period for the interferograms to be captured in a single exposure of an image capture device such as a CCD array. Each interferogram has a unique carrier frequency dependent on the angle between a respective pair of sample and reference wavefronts. In certain embodiments multiple sample and/or reference wavefronts are generated using scanning mirrors, while in other embodiments utilizing multi-wavelength beams multiple sample and/or reference wavefronts are generated with wavelength dispersive elements. The methods and apparatus are suitable for measuring aberrations at one or more positions on the retina of an eye.

23 Claims, 11 Drawing Sheets

(51) Int. Cl.
- A61B 3/10 (2006.01)
- G01B 9/02 (2006.01)
- G01J 9/02 (2006.01)
- A61B 3/117 (2006.01)
- A61B 3/107 (2006.01)
- G02B 27/10 (2006.01)
- G02B 27/28 (2006.01)
- G02C 7/02 (2006.01)

(52) U.S. Cl.
CPC ............ *A61B 3/1025* (2013.01); *A61B 3/117* (2013.01); *A61B 3/14* (2013.01); *G01B 9/02027* (2013.01); *G01B 9/02039* (2013.01); *G01B 9/02041* (2013.01); *G01B 9/02044* (2013.01); *G01B 9/02091* (2013.01); *G01J 9/02* (2013.01); *G02B 27/1013* (2013.01); *G02B 27/283* (2013.01); *G01B 2290/70* (2013.01); *G01J 2009/0219* (2013.01); *G01J 2009/0238* (2013.01); *G02C 7/027* (2013.01); *G02C 2202/24* (2013.01)

(56) References Cited

U.S. PATENT DOCUMENTS

| | | |
|---|---|---|
| 8,348,427 B2 | 1/2013 | Buckland |
| 2011/0134436 A1 | 6/2011 | Podoleanu |
| 2011/0211162 A1 | 9/2011 | Thibos |
| 2013/0010257 A1 | 1/2013 | Primeau |

OTHER PUBLICATIONS

Dubra et al 'Double lateral shearing interferometer for the quantitative measurement of tear film topography' Appl Opt 44 (2005) 1191-1199.

Kühn et al 'Real-time dual-wavelength digital holographic microscopy with a single hologram acquisition' Opt Exp 15 (2007) 7231-7242.

Cerviño et al 'Clinical ocular wavefront analyzers' J Refract Surgery 23 (2007) 603-616.

Jaeken & Artal 'Optical quality of emmetropic and myopic eyes in the periphery measured with high-angular resolution' Invest Ophthal & Visual Science 53 (2012) 3405-3413.

Jaeken et al 'Comparison of two scanning instruments to measure peripheral refraction in the human eye' J Opt Soc Am A 29 (2012) 258-264.

Velghe et al 'Wave-front reconstruction from multidirectional phase derivatives generated by multilateral shearing interferometers' Opt Lett 30 (2005) 245-247.

Wei & Thibos 'Design and validation of a scanning Shack Hartmann aberrometer for measurements of the eye over a wide field of view' Opt Exp 18 (2010) 1134-1143.

Girshovitz & Shaked 'Compact and portable low-coherence interferometer with off-axis geometry for quantitative phase microscopy and nanoscopy' Opt Exp 21 (2013) 5701-5714.

Lue et al 'Single-shot quantitative dispersion phase microscopy' Appl Phys Lett 101 (2012) 084101.

Min et al 'Dual-wavelength slightly off-axis digital holographic microscopy' Appl Opt 51 (2012) 191-196.

Onodera & Ishii 'Two-wavelength interferometry that uses a Fourier-transform method' Appl Opt 37 (1998) 7988-7994.

Siedlecki et al 'Dynamic changes in corneal topography and its influence on the point-spread function of the eye' Appl Opt 46 (2007) 1361-1366.

Watanabe et al 'High-speed linear detection time domain optical coherence tomography with reflective grating-generated spatial reference delay' Appl Opt 48 (2009) 3401-3406.

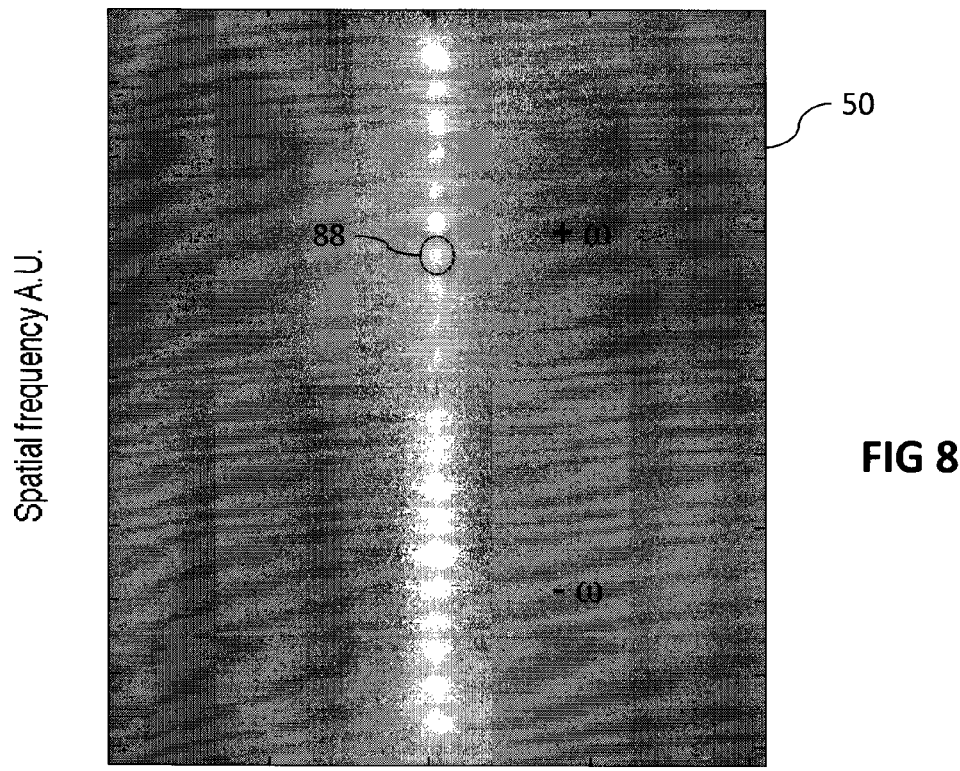
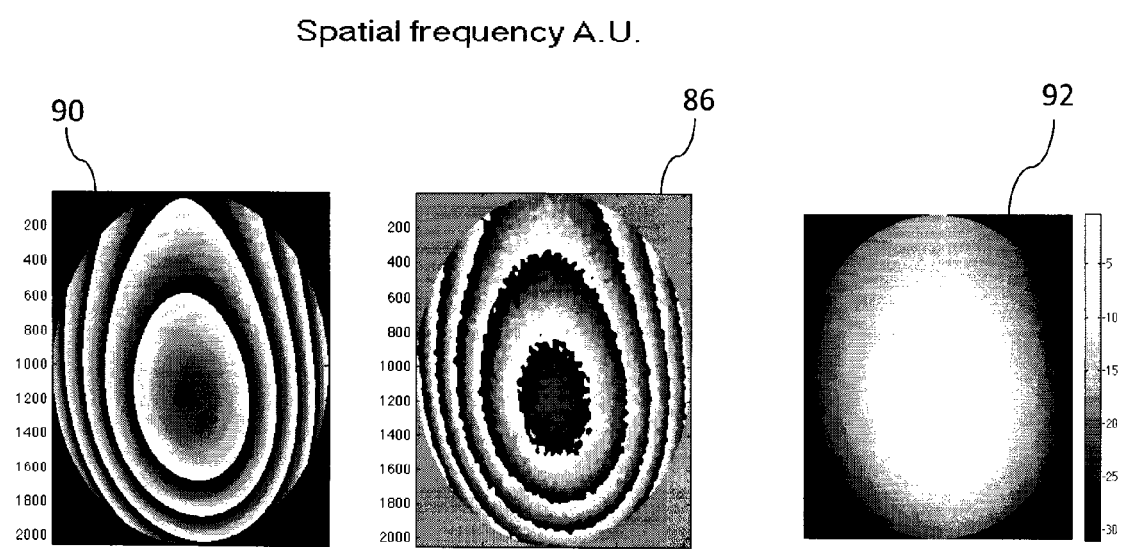
FIG 8
FIG 9
FIG 10

WAVEFRONT ANALYSER

FIELD OF THE INVENTION

The invention relates to interferometric techniques for rapidly analysing one or more wavefronts obtained from a sample. The invention has been developed primarily for analysis of ocular wavefronts and will be described hereinafter with reference to this application. However it will be appreciated that the invention is not limited to this particular field of use.

RELATED APPLICATIONS

The present application claims priority from Australian Provisional Patent Application No 2013902254 entitled 'Ocular metrology employing spectral wavefront analysis of reflected light', filed on 20 Jun. 2013, the contents of which are incorporated herein by reference.

BACKGROUND OF THE INVENTION

Any discussion of the prior art throughout the specification should in no way be considered as an admission that such prior art is widely known or forms part of the common general knowledge in the field.

Measurements of optical components and in particular the human eye have been addressed by a range of different instruments which have been able to provide information regarding different aspects of the eye's morphology and function as well as identification of various anomalies. The Shack-Hartmann technique is perhaps the most widely used method for measuring ocular wavefront aberrations. As shown in schematic form in FIG. 1, an incoming known beam 2 is transmitted through a beam splitter 4 to an eye under test 6, where the beam is focused by the eye's optical power 8 onto or close to the retina 10. A small reflected component is then collimated by the eye's optical power and separated from the incoming beam 2 by the beam splitter 4 to form an outgoing wavefront 12 which contains information on residual optical power and aberrations of the eye 6. The outgoing wavefront 12 is analysed with a Shack-Hartmann analyser 14 which, as shown in the enlargement in FIG. 1a, consists of a micro lens array 16 that samples the wavefront across a predetermined grid and focuses it onto a focal plane array 18. The positions of the image spots 20 from each micro lens can be used to estimate the slope 22 of wavefront 12 at each sampling point. If the slopes can be determined with sufficient accuracy and if the changes between the sampling points are not too great then it is possible to reconstruct the actual phase 24 of the wavefront at each of the sampling points. An advantage of the Shack-Hartmann technique is that it is self-referencing, improving robustness. A drawback is that as the wavefront slope becomes larger the image spots 20 begin to overlap, which limits the maximum level of aberration that can be measured. Furthermore the sampling resolution is limited by the micro lens array 16, which may for example comprise 30×30 micro lenses on a 250 μm pitch.

Interest in peripheral vision has been increasing in recent years, partly because of the suggestion that it may influence eye growth and myopia development. A scanning implementation of the Shack-Hartmann technique has been reported by Jaeken et al (Optics Express 19(8), 7903-7913, 11 Apr. 2011), capable of measuring over 80 degrees of visual field with 1 degree resolution in 1.8 s. Although relatively fast, this scanning method may still be compromised by changes in the subject eye during the measurement time, and it also suffers from the general limitations of the Shack-Hartmann technique described above.

In the shearing interferometry technique (Dubra et al Applied Optics 44(7), 1191-1199, 1 Mar. 2005) the gradient of a wavefront is inferred from the interference of laterally shifted copies of the wavefront. Like the Shack-Hartmann technique, shearing interferometry is a robust self-referential approach suitable for ocular examination and has the advantage of higher spatial resolution. Whilst simple in principle, the implementation is complicated by the requirement for the wavefront gradient to be measured simultaneously in more than one direction, see for example Kühn et al (Optics Express 15(2), 7231-7242, 11 Jun. 2007) which describes the use of a holographic grating structure to produce shifted copies of a wavefront in orthogonal lateral directions. Although these approaches are robust to patient movement they are reliant on the interference of two copies of the sample signal. This causes little difficulty if the sample signals are relatively intense, as in the specular corneal tear film reflections analysed in Dubra et al for example, but is of much greater concern when measuring the considerably weaker retinal reflections.

OBJECT OF THE INVENTION

It is an object of the present invention to overcome at least one of the limitations of the prior art. It is an object of the present invention in its preferred form to provide apparatus and methods for rapidly analysing one or more wavefronts obtained from a sample, via the formation and analysis of two or more interferograms with unique carrier frequencies.

SUMMARY OF THE INVENTION

According to one aspect of the present invention there is provided an apparatus for analysing one of more wavefronts from a sample, said apparatus comprising an interferometer and an image capture device, said interferometer being adapted to:
  split an incoming light field into a sample beam and a reference beam, thereby defining a sample arm and a reference arm;
  direct said sample beam onto a sample to form one or more wavefronts from said sample;
  separate said reference beam into two or more reference wavefronts; and
  mix said one or more sample wavefronts with said two or more reference wavefronts to form two or more interferograms on said image capture device, wherein each interferogram has a unique carrier frequency dependent on a respective angle between a sample wavefront and a reference wavefront, and wherein said interferometer is adapted to form said two or more interferograms in a sufficiently short time period for said image capture device to capture said interferograms in a single exposure.

In preferred embodiments the respective angles are determined by the propagation directions of the two or more reference wavefronts.

In certain embodiments the incoming light field comprises two or more distinct wavelength components.

The reference arm preferably comprises a first wavelength dispersive element for separating the reference beam into two or more reference wavefronts on the basis of the wavelength components. Preferably the sample arm comprises a second wavelength dispersive element for directing the sample beam onto two or more regions of the sample on the basis of the wavelength components, to form two or more sample wavefronts. In preferred embodiments the second wavelength dispersive element is adapted to combine two or more sample wavefronts reflected from the sample such that the sample wavefronts propagate along a common path towards the image capture device.

In certain embodiments the first wavelength dispersive element is adapted to scan the reference beam in the direction normal to its dispersive axis, to provide a two dimensional grid of carriers in the frequency domain. In other embodiments the reference arm comprises a scanning mirror adapted to scan the reference beam in the direction normal to the dispersive axis of the first wavelength dispersive element, to provide a two dimensional grid of carriers in the frequency domain.

In certain embodiments the first wavelength dispersive element is adapted to scan the reference beam in the direction normal to its dispersive axis to provide a two dimensional grid of carriers in the frequency domain, and the sample arm is adapted to scan the sample beam in the direction normal to the dispersive axis of the second wavelength dispersive element, wherein the scanning of the sample beam is synchronous with the scanning of the reference beam. In other embodiments the reference arm comprises a scanning mirror adapted to scan the reference beam in the direction normal to the dispersive axis of the first wavelength dispersive element, and the sample arm is adapted to scan the sample beam in the direction normal to the dispersive axis of the second wavelength dispersive element, wherein the scanning of the sample beam is synchronous with the scanning of the reference beam. In certain embodiments the second wavelength dispersive element is adapted to scan the sample beam in the direction normal to its dispersive axis. In other embodiments the sample arm comprises a scanning mirror adapted to scan the sample beam in the direction normal to the dispersive axis of the second wavelength dispersive element.

The incoming light field is preferably provided by a pulsed light source having a pulse window time that is substantially shorter than a period with which the reference beam or sample beam is scanned.

In preferred embodiments the sample arm comprises an optical system for tuning the range of angles through which the second wavelength dispersive element directs the sample beam onto the sample. The optical system preferably comprises a micro lens array for performing a numerical aperture conversion.

In certain embodiments the sample arm comprises a first scanning element for directing the sample beam onto two or more regions of the sample in sequence, and the first wavelength dispersive element is adapted to scan the reference beam in the direction normal to its dispersive axis, synchronously with respect to the first scanning element, to provide a two dimensional grid of carriers in the frequency domain. The first scanning element is preferably adapted to combine two or more sample wavefronts reflected from the sample such that the sample wavefronts propagate along a common path towards the image capture device.

Preferably the incoming light field is provided by a pulsed light source having a pulse window time that is substantially shorter than a scan period of the first scanning element, or substantially shorter than a period with which the reference beam is scanned.

In preferred embodiments the first scanning element comprises a MEMS mirror.

In preferred embodiments the sample arm comprises an optical system for tuning the range of angles through which the first scanning element directs the sample beam onto the sample. Preferably, the optical system comprises a micro lens array for performing a numerical aperture conversion.

In certain embodiments the incoming light field comprises a first wavelength component.

Preferably, the reference arm comprises a second scanning element adapted to be scanned in one or two axes, for separating the reference beam into two or more reference wavefronts. The second scanning element preferably comprises a MEMS mirror.

The sample arm preferably comprises a first scanning element adapted to be scanned in one or two axes for directing the sample beam onto two or more regions of the sample to form two or more sample wavefronts, wherein the scanning of the first and second scanning elements is synchronous in at least one axis. In preferred embodiments the first scanning element is adapted to combine two or more sample wavefronts reflected from the sample such that the sample wavefronts propagate along a common path towards the image capture device. In certain embodiments the first scanning element is adapted to be scanned in one axis, and the second scanning element is adapted to be scanned in one axis, synchronously with respect to the first scanning element. In other embodiments the first scanning element is adapted to be scanned in one axis, and the second scanning element is adapted to be scanned in two axes, synchronously with respect to the first scanning element. In yet other embodiments the first scanning element is adapted to be scanned in one axis, and the second scanning element is adapted to be scanned synchronously with respect to the first scanning element in one axis and more rapidly in a second axis.

In preferred embodiments the first scanning element comprises a MEMS mirror. The sample arm preferably comprises an optical system for tuning the range of angles through which the first scanning element directs the sample beam onto the sample. Preferably, the optical system comprises a micro lens array for performing a numerical aperture conversion.

In preferred embodiments the incoming light field is provided by a pulsed light source having a pulse window time that is substantially shorter than a scan period of the first or second scanning element.

The apparatus preferably comprises a processor for analysing the two or more interferograms to extract phase information from each of the one or more sample wavefronts.

In certain embodiments the interferometer comprises non-polarising means for splitting the incoming light field into the sample and reference beams, and the reference arm comprises polarisation dispersive optics for separating the reference beam into two or more reference wavefronts. The polarisation dispersive optics preferably comprise a wedged polarisation walk-off plate and a $\frac{1}{8}$ waveplate. Preferably, the sample arm comprises a quarter waveplate for changing the polarisation state of the sample beam from linear to circular. The apparatus preferably comprises a processor for analysing the two or more interferograms to obtain amplitude and phase information from respective wavefronts, and subsequently determine a map of polarisation state across each of the one or more sample wavefronts.

According to a second aspect of the present invention there is provided a method for analysing one of more wavefronts from a sample, said method comprising the steps of:

splitting an incoming light field into a sample beam and a reference beam;

directing said sample beam onto a sample to form one or more wavefronts from said sample;

separating said reference beam into two or more reference wavefronts;

mixing said one or more sample wavefronts with said two or more reference wavefronts to form two or more interferograms on an image capture device in a sufficiently short time period for said image capture device to capture said interferograms in a single exposure, wherein each interferogram has a unique carrier frequency dependent on a respective angle between a sample wavefront and a reference wavefront; and processing said two or more interferograms to extract phase information from each of said one or more sample wavefronts.

In preferred embodiments the respective angles are determined by the propagation directions of the two or more reference wavefronts.

In certain embodiments the incoming light field comprises two or more distinct wavelength components.

Preferably, the reference beam is separated into two or more reference wavefronts using a first wavelength dispersive element. The sample beam is preferably directed onto two or more regions of the sample using a second wavelength dispersive element, to form two or more sample wavefronts. The second wavelength dispersive element preferably combines two or more sample wavefronts reflected from the sample such that the sample wavefronts propagate along a common path towards the image capture device.

In certain embodiments the first wavelength dispersive element scans the reference beam in the direction normal to its dispersive axis, to provide a two dimensional grid of carriers in the frequency domain. In other embodiments a scanning mirror scans the reference beam in the direction normal to the dispersive axis of the first wavelength dispersive element, to provide a two dimensional grid of carriers in the frequency domain.

In certain embodiments the first wavelength dispersive element scans the reference beam in the direction normal to its dispersive axis to provide a two dimensional grid of carriers in the frequency domain, and the sample beam is scanned in the direction normal to the dispersive axis of the second wavelength dispersive element, wherein the scanning of the sample beam is synchronous with the scanning of the reference beam. In alternative embodiments a scanning mirror scans the reference beam in the direction normal to the dispersive axis of the first wavelength dispersive element, and the sample beam is scanned in the direction normal to the dispersive axis of the second wavelength dispersive element, wherein the scanning of the sample beam is synchronous with the scanning of the reference beam.

In certain embodiments the second wavelength dispersive element scans the sample beam in the direction normal to its dispersive axis. In alternative embodiments a scanning mirror scans the sample beam in the direction normal to the dispersive axis of the second wavelength dispersive element.

The incoming light field is preferably provided by a pulsed light source having a pulse window time that is substantially shorter than a period with which the reference beam or sample beam is scanned.

In certain embodiments the method further comprises the step of tuning the range of angles through which the second wavelength dispersive element directs the sample beam onto the sample. In certain embodiments the method further comprises the step of performing a numerical aperture conversion.

In certain embodiments the sample beam is directed onto two or more regions of the sample in sequence using a first scanning element, and the first wavelength dispersive element scans the reference beam in the direction normal to its dispersive axis, synchronously with respect to the first scanning element, to provide a two dimensional grid of carriers in the frequency domain. The first scanning element preferably combines two or more sample wavefronts reflected from the sample such that the sample wavefronts propagate along a common path towards the image capture device.

The incoming light field is preferably provided by a pulsed light source having a pulse window time that is substantially shorter than a scan period of the first scanning element, or substantially shorter than a period with which the reference beam is scanned.

In preferred embodiments the first scanning element comprises a MEMS mirror. Preferably, the method further comprises the step of tuning the range of angles through which the first scanning element directs the sample beam onto the sample. In certain embodiments the method further comprises the step of performing a numerical aperture conversion.

In certain embodiments the incoming light field comprises a first wavelength component.

The reference beam is preferably separated into two or more reference wavefronts using a second scanning element scanned in one or two axes. Preferably, the second scanning element comprises a MEMS mirror.

In certain embodiments the sample beam is directed onto two or more regions of the sample, to form two or more wavefronts, using a first scanning element scanned in one or two axes, wherein the scanning of the first and second scanning elements is synchronous in at least one axis. The first scanning element preferably combines two or more sample wavefronts reflected from the sample such that the sample wavefronts propagate along a common path towards the image capture device. In certain embodiments the first scanning element is scanned in one axis, and the second scanning element is scanned in one axis, synchronously with respect to the first scanning element. In alternative embodiments the first scanning element is scanned in one axis, and the second scanning element is scanned in two axes, synchronously with respect to the first scanning element. In yet other embodiments the first scanning element is scanned in one axis, and the second scanning element is scanned synchronously with respect to the first scanning element in one axis and more rapidly in a second axis.

In preferred embodiments the first scanning element comprises a MEMS mirror. Preferably, the method further comprises the step of tuning the range of angles through which the first scanning element directs the sample beam onto the sample. In certain embodiments the method further comprises the step of performing a numerical aperture conversion.

In preferred embodiments the incoming light field is provided by a pulsed light source having a pulse window time that is substantially shorter than a scan period of the first or second scanning element.

In certain embodiments the splitting step is performed using non-polarising means, and the reference beam is separated into two or more reference wavefronts using polarisation dispersive optics. The polarisation dispersive optics preferably comprise a wedged polarisation walk-off plate and a ⅛ waveplate. Preferably, the method further comprises the step of changing the polarisation state of the sample beam from linear to circular. Preferably, the processing step further comprises extracting amplitude information from each of the one or more sample wavefronts and using both phase and amplitude information to determine a map of polarisation state across each of the one or more sample wavefronts.

According to a third aspect of the present invention there is provided an article of manufacture comprising a computer usable medium having a computer readable program code configured to operate the apparatus according to the first aspect, or to implement the method according to the second aspect.

BRIEF DESCRIPTION OF THE DRAWINGS

Preferred embodiments of the invention will now be described, by way of example only, with reference to the accompanying drawings in which:

FIG. 8 shows a simulated 2D FFT of a composite interferogram obtained for ten wavefronts with the apparatus of FIG. 3;

FIG. 9 shows the down-converted wrapped wavefront extracted from a selected carrier in the simulated 2D FFT of FIG. 8, in comparison with the expected wrapped wavefront;

FIG. 10 shows the unwrapped wavefront obtained by applying a phase unwrapping algorithm to the down-converted wrapped wavefront of FIG. 9;

DETAILED DESCRIPTION OF THE INVENTION

Figure 1:
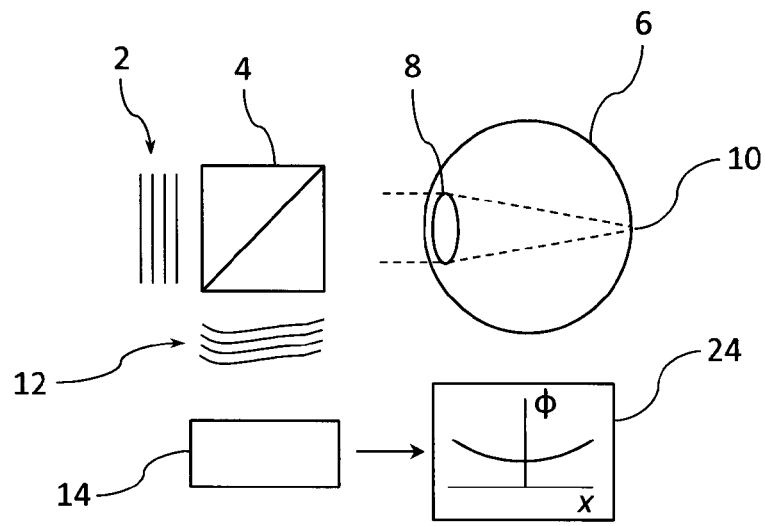
FIG. 1 illustrates in schematic form a Shack-Hartmann wavefront analyser for determining wavefront aberrations of an eye.
Figure 1A:
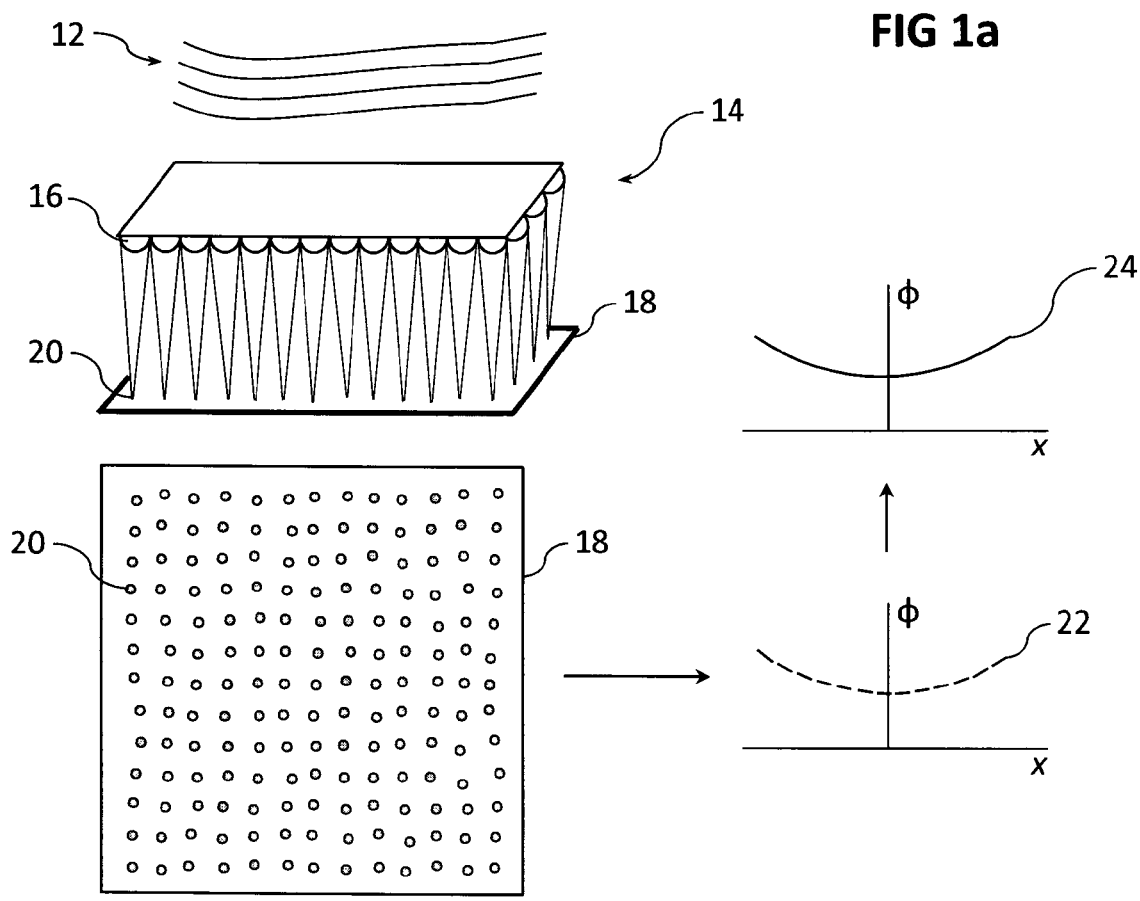
FIG. 1a illustrates in expanded view a portion of the wavefront analyser of FIG. 1.
Figure 2:
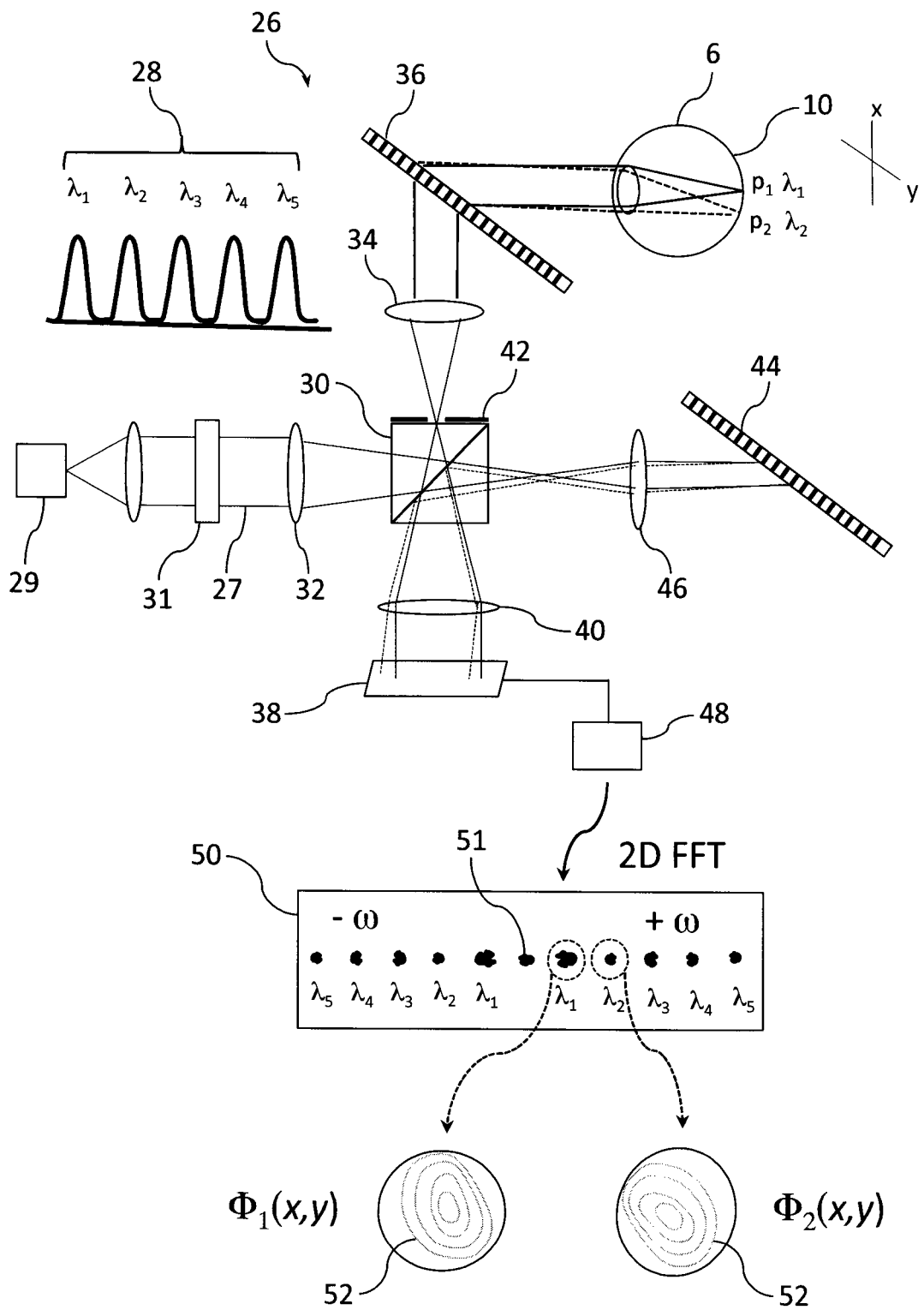
FIG. 2 illustrates an apparatus for analysing one or more wavefronts from an eye according to a first embodiment of the invention.

Simultaneous Wavefront Measurements at Multiple Fields of View with a Multi-Wavelength Source FIG. 2 illustrates an apparatus 26 for analysing one or more wavefronts from a sample according to a first embodiment of the present invention. In this embodiment an incoming light field comprising a collimated beam 27 with multiple distinct narrow wavelength band components 28, formed for example from a broad wavelength low coherence optical source 29 filtered by an etalon 31 to produce a comb of wavelengths 28, is used to measure simultaneously the aberrations from multiple points $p_1$, $p_2$ etc on the retina 10 of an eye 6. In the illustrated example the incoming collimated beam 27 has five narrow band components $\lambda_1 \ldots \lambda_5$ although in practice there may for example be between ten and thirty wavelength components, which may for example have bandwidths in the range of 0.005 to 0.3 nm. The apparatus 26 is based on a Twyman-Green interferometer in which a beam splitter 30 splits an incoming collimated beam 27 into a sample beam and a reference beam, with the sample beam directed by a 4F optical system comprising relay lenses 32 and 34 onto a wavelength dispersive element in the form of a transmissive diffraction grating 36. In alternative embodiments the wavelength dispersive element may be a reflective diffraction grating or a prism. The diffraction grating 36 diffracts the multi-wavelength sample beam such that each wavelength component has a unique field of view angle onto the pupil of the eye 6. Each collimated wavelength component is then focused by the eye to a spot on the retina 10, with each spot $p_n$ being associated with a wavelength component $\lambda_n$. With five distinct wavelength components as shown, five separate spots on the retina will be illuminated simultaneously, although for clarity only two are depicted. Preferably the diameter of the collimated incident beam is limited to ensure the incident beam path is minimally affected by aberrations of the eye. Ideally the incident beam forms a diffraction limited spot on the retina. This may not be achievable with a severely myopic eye, in which case a partially corrective lens may be required.

A portion of the light incident on each spot $p_n$ is reflected back towards the diffraction grating 36, being subjected to aberrations from the eye on the outward path. The reciprocity of the system ensures that on their return paths the aberrated wavefronts from the various retinal spots $p_n$ propagate parallel to each other towards the lens 34. The aberrated wavefronts are transmitted through the beam splitter 30 and projected onto an image capture device 38 that may for example be a two dimensional CCD or CMOS photodetector array, via a 4F optical system comprising lenses 34, 40 and an optional aperture 42. The aperture, if present, is preferably circular with size chosen so as to limit the frequency content of the aberrated sample wavefronts, thereby minimising crosstalk between wavefronts. In practice this limits the maximum aberration measurable. The optimal size of the aperture will depend on the number of sample wavefronts being measured simultaneously.

Turning now to the reference arm of the Twyman-Green interferometer, the reference beam from the beam splitter 30 is incident on a wavelength dispersive element in the form of a reflective diffraction grating 44, which separates the reference beam into a plurality of reference wavefronts based on its distinct wavelength components $\lambda_1$, $\lambda_2$ etc. The diffracted reference wavefronts are projected onto the image capture device 38 via a 4F optical system comprising lenses 40, 46 and reflection at the beam splitter 30, with angle of incidence determined by the wavelength of each wavefront and the period of the grating 44. The lenses 40, 46 are chosen such that the diameter of each of the reference wavefronts at the image capture device 38 is of similar size or larger than that of the sample wavefronts reflected from the eye under test 6.

In the absence of aberrations each sample wavefront reflected from the eye 6 mixes with the reference field of its corresponding wavelength to produce an interferogram or fringe pattern with a well-defined spatial period determined by the wavelength and the angle between the sample and reference wavefronts. In this apparatus these angles are determined by the angle of incidence, or equivalently the propagation direction, of each reference wavefront. For the purposes of this specification the frequency associated with the spatial period will be referred to as the spatial carrier frequency of the wavefront. The optical path length difference between the reference and sample arms may be selected by adjusting the position of the reference arm grating 44. In the particular embodiment shown in FIG. 2 the optical source is a broad wavelength source 29 filtered by an etalon 31 to produce a comb of narrow band components 28, which may for example have bandwidths in the range of 0.005 to 0.3 nm. Using narrower band components increases the coherence length but can cause problems with loss of signal power and increased speckle pattern interference.

In preferred embodiments the period of the reference arm grating 44 is chosen to optimise the distribution of the spatial carrier frequencies that falls within the Nyquist limit of the photodetector array 38. The maximum carrier frequency is preferably chosen such that its associated period is greater than two pixels on the photodetector array, while the minimum carrier frequency is preferably chosen to be higher than the expected maximum aberration frequency within the aberrated sample wavefronts.

Although the apparatus of FIG. 2 uses a conventional power beam splitter 30, it will be appreciated by those skilled in the art that a polarisation beam splitter with associated polarisation optics, as described below with reference to FIG. 12 for example, could be used instead. One potential benefit of employing a polarisation interferometer is the reduction of unwanted reflections from lenses and other optical components.

In the embodiment shown in FIG. 2 the multiple interferograms are produced simultaneously on the photodetector array 38, enabling acquisition of information from a plurality of spots $p_1$, $p_2$ etc on the retina 10 in a single exposure (i.e. 'single shot' acquisition). Preferably the multiple interferograms are captured by the photodetector array in around 1 ms or less to avoid phase wash out associated with patient movement. The number of spots is determined by the number of discrete wavelength components 28 in the incoming beam 27, which may for example be from ten to thirty although for illustrative purposes we will consider an incoming beam with five discrete wavelength components 28 producing five interferograms on the photodetector array. In the presence of aberrations the spatial frequency content of each sample wavefront mixes with that of its carrier to produce a broadening of its carrier frequency components. An analysis of each broadened carrier component thereby enables each component wavefront to be measured. The output of the photodetector array 38 is passed to a processor 48 having machine readable code suitable for analysing the interferograms using a Fourier transform technique to calculate the amplitude and/or phase of the individual sample wavefronts, as described below.

To extract the phase information from each sample wavefront a 2D fast Fourier transform (FFT) of the composite interferogram, i.e. the combination of the five individual interferograms in this particular case, is performed after first subtracting out background terms, i.e. the self-interference of the reference and sample arms. Since the composite interferogram is real, both positive and negative frequency terms for each carrier will be evident in the calculated 2D-FFT 50. The wavefronts are distinguishable in the frequency domain because of their distinct spatial carrier frequencies. In this particular example we have eleven frequency components in the 2D-FFT 50, comprising a DC component 51 and positive and negative frequency components for each of the five wavefronts. The positive and negative frequency terms contain redundant information and either can be analysed; in this example we choose to analyse the positive frequency components. A 2D bandpass filter is applied to each positive frequency component in turn. The bandwidth of the filter is chosen to ensure minimal crosstalk between channels, as illustrated by the dashed circles centred on the first two positive frequency carriers. After filtering, the carrier frequency component of the wavefront being analysed is removed by down-converting the FFT. An inverse fast Fourier transform (IFFT) is then applied to extract the complex wavefront, from which the wrapped phase is extracted.

A phase unwrapping algorithm such as a branch cut algorithm is used to remove the $2\pi$ ambiguity to yield a two dimensional map of the phase for each individual carrier as illustrated by the schematic contour plots 52. Aberrations for each sample wavefront may be evaluated conveniently by expressing the phase map of the wavefront in terms of the sum of Zernike polynomials. The orthogonal property of Zernike polynomials over a unit circle is used to extract the Zernike coefficients.

Increasing the number of wavelength components in the incoming beam 27, and therefore the number of wavefronts, reduces the spatial bandwidth available to each wavefront. Assuming that the primary defocus aberration has the highest frequency content we find that the maximum level of primary defocus D measurable for each sample point $p_n$ is given by $$D = \frac{m\lambda}{4r_p \Delta x (N + 0.5)}$$

where $\lambda$ is the mean wavelength, m is the magnification between the pupil and the photodetector array, $r_p$ is the radius over which the wavefront is measured, N is the number of wavefronts and $\Delta x$ is the pixel spacing along the axis in which the N wavefronts are multiplexed. For N=10, m=2.0, $\lambda$=810 nm, $r_p$=2.5 mm and $\Delta x$=4.6 µm we obtain D=3.5 diopters assuming all wavefronts have equal distortion. Methods of increasing the range of the measurement include increasing the number of pixels in the camera 38, i.e. decreasing $\Delta x$, and increasing the magnification m. Alternatively, decreasing the pupil size or the sample beam radius to 4 mm (i.e. $r_p$=2 mm) increases D to 4.4 diopters per wavefront for N=10, at the expense of reduced signal power.

We now discuss simulation results for a case with N=10, where for illustrative purposes we have randomly selected second order Zernike coefficients with values between −3 and +3 and third order components between −0.5 and +0.5 (in units of wavelengths as usual). We assumed a shot noise limited system with a total input power of 1 mW and −60 dB reflectivity at the retina, and a 5 mm diameter wavefront imaged onto 2048×2048 pixel photodetector array.

The absolute value of the 2D FFT 50 of the total interferogram for the ten wavefronts is shown in FIG. 8, while FIG. 9 shows the down-converted wrapped wavefront 86 for a representative carrier 88 compared with the expected wavefront 90. The specific Zernike coefficients for this case were $a_2^0$-1.0, $a_2^1$=−0.15, $a_2^{-1}$=0.45, $a_3^1$=−0.22, $a_3^{-1}$=−0.02, $a_3^3$=0.11 and $a_3^{-3}$=−0.16. The noise in the extracted wavefront 86 is due to shot noise. Finally, the unwrapped wavefront 92 is shown in FIG. 10. The shot noise induced error in each calculated Zernike coefficient is less than 1%.

Figure 3:
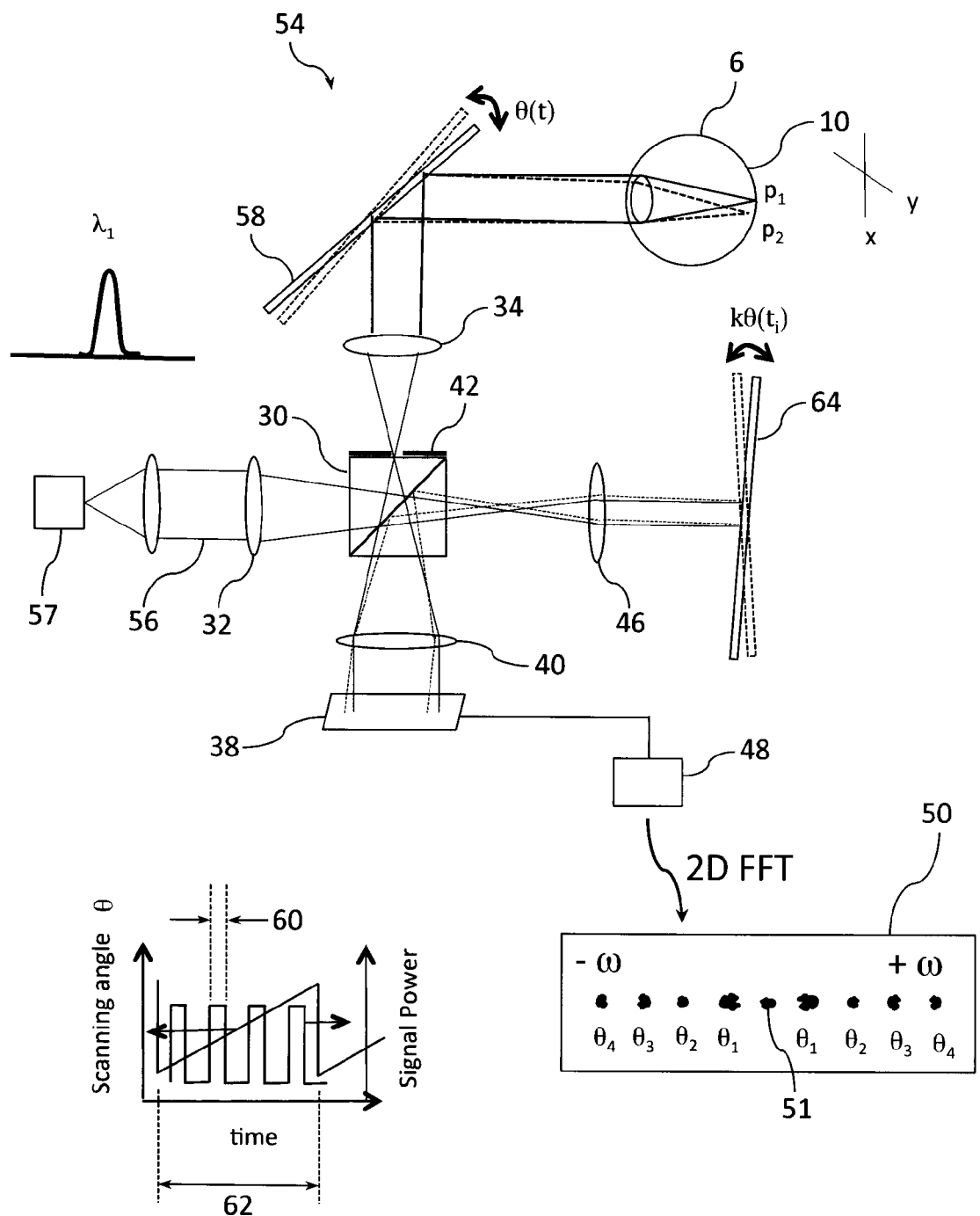
FIG. 3 illustrates an apparatus for analysing one or more wavefronts from an eye according to a second embodiment of the invention.

Fast Wavefront Measurements at Multiple Fields of View with a Single Wavelength Source FIG. 3 illustrates an apparatus 54, again based on a Twyman-Green interferometer, for analysing one or more wavefronts from a sample according to a second embodiment of the present invention. In this embodiment an incoming light field comprising a collimated beam 56 from a relatively narrow bandwidth source 57 is used to measure the aberrations from one or more spots $p_1$, $p_2$ etc on the retina 10 of an eye 6. A beam splitter 30 splits the incoming beam 56 into a sample beam and a reference beam, with the sample beam directed by a 4F optical system comprising relay lenses 32 and 34 onto a scanning element in the form of a scanning mirror 58. The scanning mirror directs the sample beam onto the pupil of the eye 6 with a time varying field of view angle. In this embodiment it is convenient to use a pulsed light source 57 such as a pulsed laser with a pulse window time 60 that is substantially shorter than the mirror scan period 62. Preferably the pulse window time 60 is of order one hundred times shorter than the mirror scan period 62. More preferably the pulse window time 60 is of order one thousand times shorter than the mirror scan period 62. In this manner the eye can be sampled at a discrete set of view angles, with the eye 6 focusing the sample beam onto a discrete set of spots $p_1$, $p_2$ etc on its retina 10. By way of example one could have twenty sample pulses each having a 50 μs window and a mirror scan period of 50 ms, thereby illuminating twenty discrete spots in 50 ms. For clarity only two spots $p_1$, $p_2$ are depicted on the retina 10 in FIG. 3.

Preferably the bandwidth of the light source 57 is sufficiently broad (i.e. not overly narrow) to limit the effects of speckle pattern interference, which is a known issue associated with narrow bandwidth sources owing to their long coherence lengths. The use of a broader single wavelength source helps to mitigate the effects of stray reflections from lenses and other elements in the optical train from corrupting the wavefront measurement. On the other hand if the single wavelength source is too broad its coherence length will reduce the maximum optical path length path difference between the reference and sample arms. A bandwidth of around 0.05 nm is a reasonable compromise between these two factors.

The light reflected from each spot $p_n$ on the retina 10 is subject to aberrations from the eye 6, and is reflected on the return path by the scanning mirror 58. The reciprocity of the system ensures that on their return paths the aberrated wavefronts of all pulses (field of view angles) propagate parallel to each other towards the lens 34. The aberrated wavefronts are transmitted through the beam splitter 30 and projected onto an image capture device 38 that may for example be a two dimensional CCD or CMOS photodetector array, via a 4F optical system comprising lenses 34, 40 and an optional aperture 42. The aperture, if present, is preferably circular, with size chosen so as to limit the maximum aberration measurable, thereby minimising crosstalk between sample wavefronts. The optimal size of the aperture will depend on the number of sample wavefronts being measured simultaneously.

Turning now to the reference arm of the Twyman-Green interferometer shown in FIG. 3, the reference beam from the beam splitter 30 is incident on a scanning element in the form of a scanning mirror 64 that is scanned synchronously with respect to the scanning mirror 58 in the sample arm. The synchronous scanning of the two scanning mirrors 58 and 64, typically achieved with some form of computer control, ensures that a unique carrier frequency is associated with the sample wavefront from each spot $p_n$ on the retina 10. The reference arm scanning mirror 64 separates the reference beam into a plurality of reflected reference wavefronts that are projected onto the image capture device 38 via a 4F optical system comprising lenses 40, 46 and reflection at the beam splitter 30, with angle of incidence determined by the angle of the scanning mirror $k\theta(t_i)$ associated with the pulse time $t_i$ of the incoming light field 56. The lenses 40, 46 are chosen such that the diameter of the reference wavefronts at the image capture device 38 is of similar size or larger than that of the sample wavefronts reflected from the eye under test 6.

With each pulse the sample wavefront reflected from a selected spot $p_n$ on the retina 10 mixes with a reflected reference wavefront to produce an interferogram or fringe pattern with a well-defined spatial period determined by the angle between the sample and reference wavefronts. In this manner, a unique carrier frequency can be mapped to each field of view angle, i.e. to each spot $p_n$ on the retina. Interference between the sample and reference wavefronts requires the optical path length difference between the sample and reference arms to be chosen to be within the coherence length of the optical source. This optical path length difference may for example be selected by adjusting the position of the reference arm scanning mirror 64.

In this embodiment a rapid sequence of interferograms are produced on the photodetector array 38 in a time period determined by the scan period, e.g. 50 ms. This time period is chosen to be sufficiently short so as to enable 'single shot' acquisition of information from a plurality of spots $p_1$, $p_2$ etc on the retina 10, i.e. acquisition in a single exposure of the photodetector array. Each individual interferogram is preferably captured by the photodetector array in around 1 ms or less to avoid phase wash out associated with patient movement, but the scanning can occur over a much longer time interval because the phase between carriers is generally not critical. There are a number of guiding factors for determining the overall period within which a sequence of interferograms can be produced and captured. These factors include the time over which the photodetector array can integrate in a single exposure and considerations of excessive background noise and patient movement. A time of 50 ms per scan is believed to be a good compromise, and is comparable to the time required for a typical Shack-Hartmann analyser to measure a single wavefront. However other scan periods, including but not limited to 10, 20, 30, 40, 60, 70, 80, 90 and 100 ms, are within the scope of the present invention.

As in the previously described embodiment, the output of the photodetector array 38 is passed to a processor 48 that calculates a 2D fast Fourier transform (FFT) 50 of the composite interferogram after first subtracting out background terms, i.e. the self-interference of the reference and sample arms. In this embodiment the 2D FFT 50 contains positive and negative frequency terms for each carrier along with a DC component 51, where each carrier corresponds to a discrete spot on the retina 10 of the eye under test 6. In this particular example there are four carriers corresponding to four spots $p_1 \ldots p_4$. The processing of the 2D FFT follows the procedure described in the previous embodiment, to yield a two dimensional map of the phase for each individual carrier.

Because the sample wavefronts emanating from different spots $p_n$ on the retina 10 are parallel when incident on the detector array 38, the angles chosen for the reference wavefronts by the scanning mirror 64 are unrelated to the angles of the sample beam incident on the eye 6 selected by the sample arm scanning mirror 58. More generally, the scan axes for the reference arm and sample arm scanning mirrors are uncoupled. This enables the spatial bandwidth of the photodetector array 38 to be utilised more efficiently by using dual axis scanning of the reference arm scanning mirror 64. For example in the variant embodiment illustrated in FIG. 4 this scanning mirror 64 is scanned in two axes as represented by the time-dependent angles $k_1\theta(t)$ and $k_2\theta(t)$ such that the spatial carrier frequencies cover a two dimensional grid in the frequency domain 50. In this particular example twelve discrete fields of view or spots $p_1 \ldots p_{12}$ on the retina 10 are covered in a single scan of the sample arm scanning mirror 58 and encoded onto twelve carrier frequencies. Since the spatial resolution of the system is dependent on the frequency spacing between the carriers, dual axis scanning of the reference arm scanning mirror 64 increases the available spatial bandwidth by $\sqrt{N}$ for a given number of N wavefronts. In practice aberrations increase at higher fields of view, so it can be advantageous to increase the spacing between carriers for higher fields of view and decrease the spacing between carriers for more central fields of view.

Similar considerations apply to the apparatus shown in FIG. 2, where a two dimensional grid of carriers in the frequency domain could be provided by scanning the reference arm grating 44 in the direction normal to its grating axis, or by providing a scanning mirror in the reference arm to scan in direction normal to the grating axis. In addition a scanning mirror could be provided in the sample arm, to either scan the y-axis (i.e. the axis normal to the dispersive axis of the sample arm grating 36) or sample more points along the x-axis. Alternatively the y-axis could be scanned by scanning the sample arm diffraction grating 36 in the direction normal to its grating axis.

Figure 5:
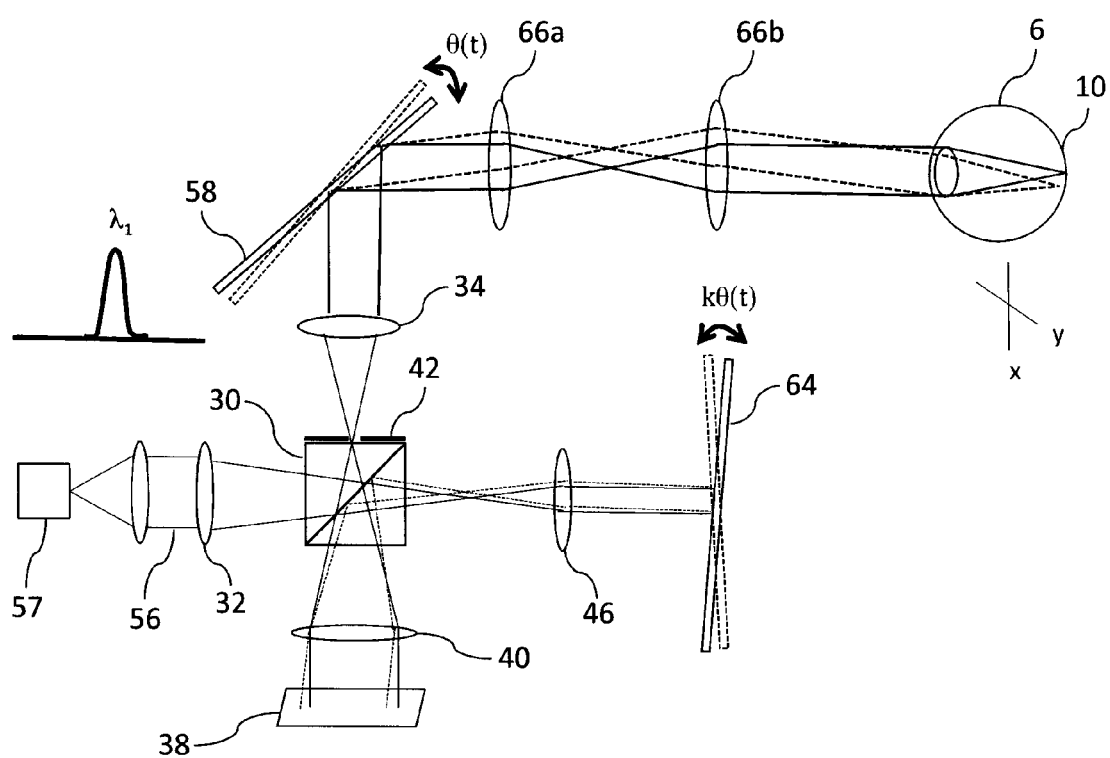
FIG. 5 illustrates another apparatus for analysing one or more wavefronts from an eye according to a second embodiment of the invention.

In yet another variant embodiment shown in FIG. 5 the apparatus comprises an additional pair of relay lenses 66a, 66b in a telescope configuration to tune the range of angles provided by the scanning mirror 58. This relay lens configuration is also applicable to the multi-wavelength embodiment shown in FIG. 2, to tune the range of angles achievable with the sample arm diffraction grating 36. This telescope configuration will be described in more detail below, with reference to FIGS. 15 and 16.

Figure 4:
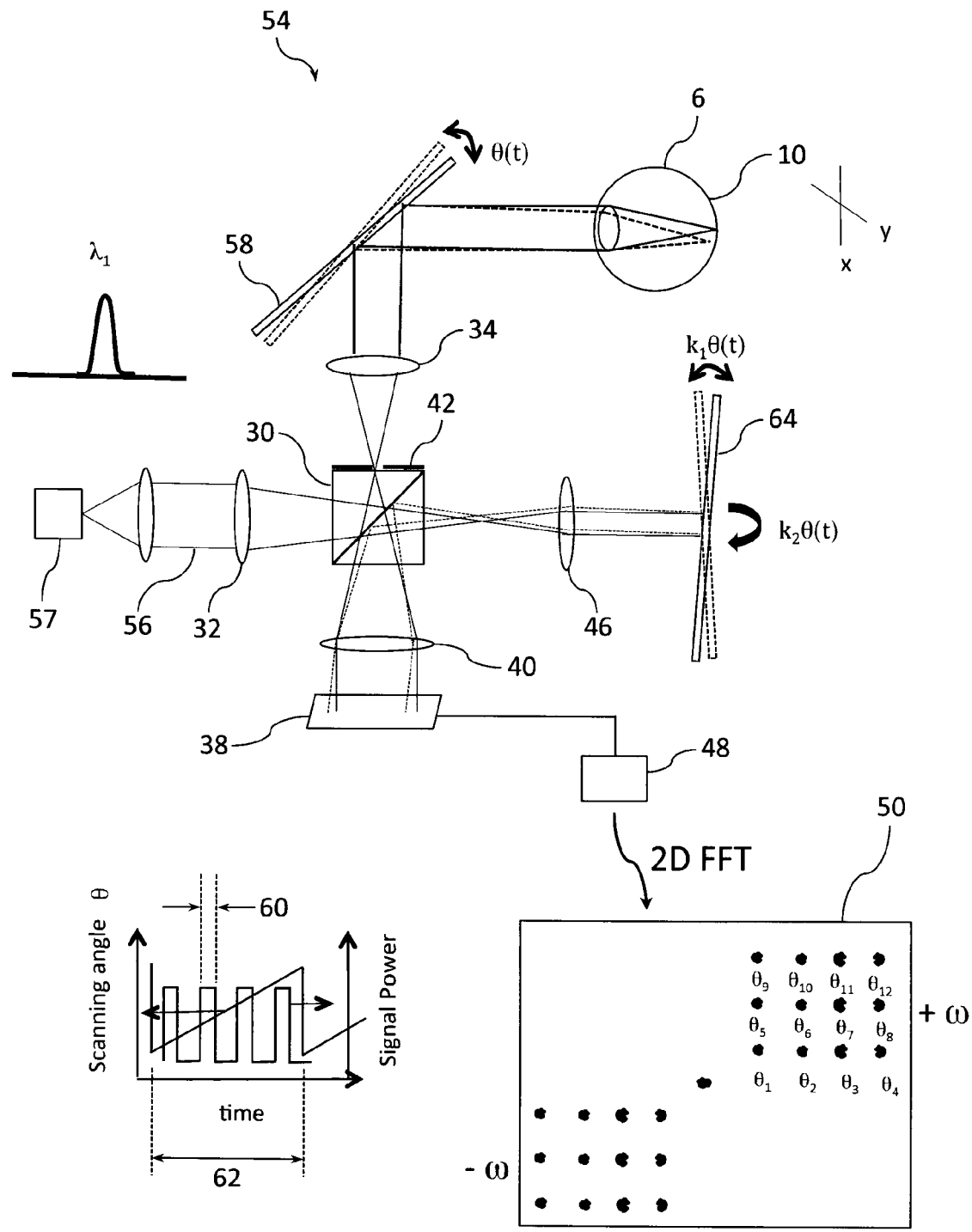
FIG. 4 illustrates another apparatus for analysing one or more wavefronts from an eye according to a second embodiment of the invention.

We note that in each of the embodiments illustrated in FIGS. 3, 4 and 5 there is no requirement for the sample arm scanning mirror 58 to be scanned in one axis only. That is, it can be scanned in one axis to illuminate a linear array of spots on the retina 10 or scanned in two axes to illuminate a two dimensional array of spots. Dual axis scanning in the sample arm can also be achieved using a sequence of two mirrors configured to be scanned in orthogonal axes. Irrespective of the arrangements of the illuminated sample spots, the reciprocity of the system ensures that the carrier frequencies of the interferograms are selected by the reference arm scanning mirror 64.

In yet another variation the sample arm could illuminate a single spot on the retina while the reference arm scans across different carrier frequencies. In this variation a wavefront from a single spot on the retina, or to be more precise two or more instances of that wavefront since it will contain time-varying noise, are interfered with two or more reference wavefronts to form a sequence of two or more interferograms with unique carrier frequencies. This enables two or more measurements from a single spot on the retina to be averaged, e.g. to improve the signal to noise ratio or reduce speckle. After acquiring sufficient wavefront data from one spot, the sample arm scanning mirror 58 can move the sample beam to illuminate a second spot on the retina, in either the same frame (i.e. the same exposure) of the photodetector array or a subsequent frame. This scanning sequence enables averaging to be applied for each of multiple spots on the retina. The reference arm scanning mirror 64 is scanned in two axes, more rapidly in one axis for averaging over individual spots on the retina and more slowly in the other axis, synchronous with the sample arm scanning mirror 58.

For cases in which two or more independent sample wavefronts are being analysed, i.e. where measurement of one sample wavefront gives no information about another sample wavefront, it is preferable for the spatial carriers to be separated by frequencies greater than that of that of the bandwidth of each carrier. With reference to FIGS. 2 and 3 for example, this means that adjacent frequency terms in the 2D FFT 50 should not overlap. This is not a strict requirement when the aberrations are slowly varying with field of view, although it does complicate the analysis.

The situation is different if the sample wavefronts being analysed are not independent, such as in the previously described example in which we generate multiple interferograms from the same field of view. It is possible for the frequency separation between spatial carriers for multiple measurements of a sample wavefront from a single visual field angle to be smaller than the bandwidth of the aberration. One possible way of dealing with overlapping carriers is to divide the complex interferogram (obtained from the Hilbert transform of the interference signal) of the aberrated wavefronts by the complex interferogram measured in the absence of aberration. Another possible approach is to treat the overlap as an optimisation problem, for example by making an initial guess at the aberrated wavefront using a model with three Zernicke coefficients and using this assumption to remove the aberration from the interferogram. This process is iterated until the blurred frequency component in the 2D FFT is reduced to the well-defined point one would expect from a non-aberrated wavefront.

Figure 11:
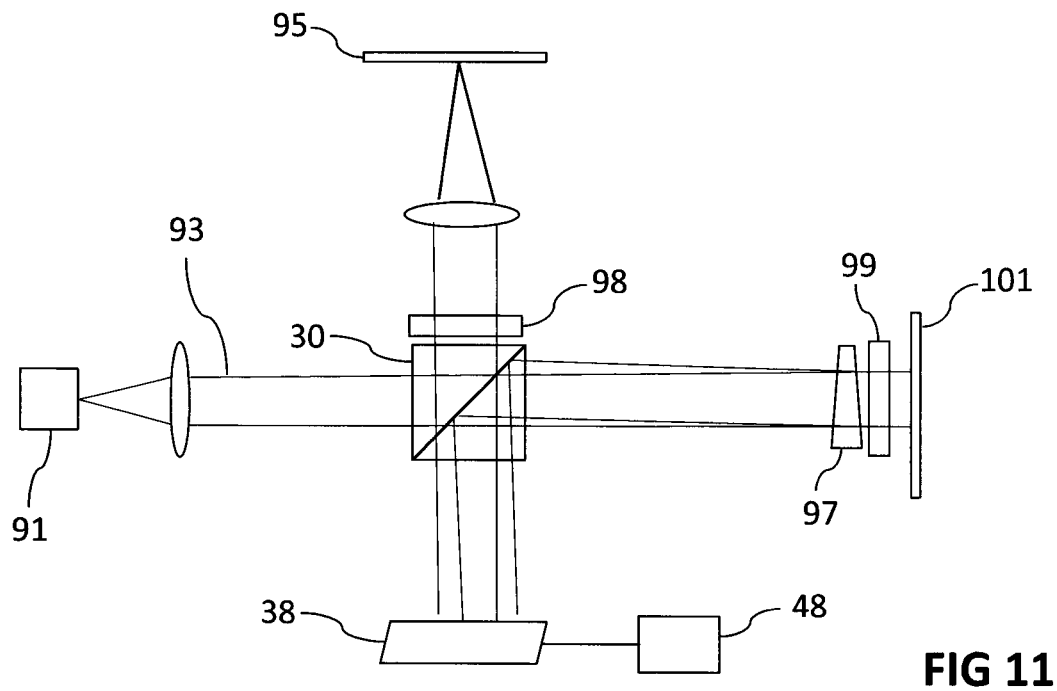
FIG. 11 illustrates a polarisation sensitive wavefront analyser according to another embodiment of the invention.

In yet another embodiment, illustrated in FIG. 11, a wavefront analyser is configured to be polarisation sensitive. In this embodiment a suitable light source 91 provides a linearly polarised beam 93 that is separated into two arms by a non-polarising beam splitter 30. In the sample arm the beam passes through a quarter waveplate 98 so that a circular polarisation state is incident upon a sample 95. The polarisation of the reflected sample wavefront will be determined by the birefringence of the sample and in general will be elliptical. We note that the quarter waveplate 98 is not necessarily required, but its presence guards against the possibility that the sample beam polarisation might be aligned with a birefringence axis of the sample, in which case there will be no change in polarisation state upon reflection. Turning now to the reference arm, the linearly polarised beam passes through a wedged polarisation walk-off plate 97 that is aligned such that the beam passes through without deflection. A ⅛ waveplate 99 between the wedged polarisation walk-off plate 97 and a mirror 101 ensures that a circular polarisation state is incident upon the wedged polarisation walk-off plate 97 on the return path. The wedged polarisation walk-off plate separates the now circularly polarised reference beam into two orthogonally polarised components that are incident on the photodetector array 38 at different angles, mixing with the sample wavefront to form simultaneously two interferograms with unique carrier frequencies. The wedged polarisation walk-off plate 97 and the ⅛ waveplate 99 have effectively acted as a system of polarisation dispersive optics, separating the reference beam into two reference wavefronts.

The output of the photodetector array 48 is sent to a processor 48 that analyses the interferograms using a Fourier transform technique similar to that described previously for extracting wavefront phase, including calculating an FFT of the composite interferogram, down-converting the filtered spatial carriers and applying an IFFT to obtain distinct wavefronts corresponding to the two polarisation components. For the polarisation analysis however, we use both phase and amplitude information obtained from the IFFT to determine a map of polarisation state across a sample wavefront. The polarisation state for particular (x, y) spatial components of the sample wavefront can for example be described by Jones vectors or Stokes vectors.

If several sample wavefronts are to be analysed, the static reference arm mirror 101 can be replaced by a scanning mirror 64 as in FIG. 3 or by a diffraction grating 44 as in FIG. 2, depending on the wavelength makeup of the input light field. In either case the scanning or wavelength dispersion axis should be orthogonal to the polarisation dispersion axis. Irrespective of whether this polarisation-sensitive embodiment is used in a scanning or wavelength dispersive apparatus, individual sample interferograms are preferably captured in around 1 ms or less to avoid phase wash out. We note that it is also possible to include polarisation dispersive optics, i.e. a wedged walk-off plate 97 and a ⅛ waveplate 99, in the sample arm of the interferometer.

Figure 12:
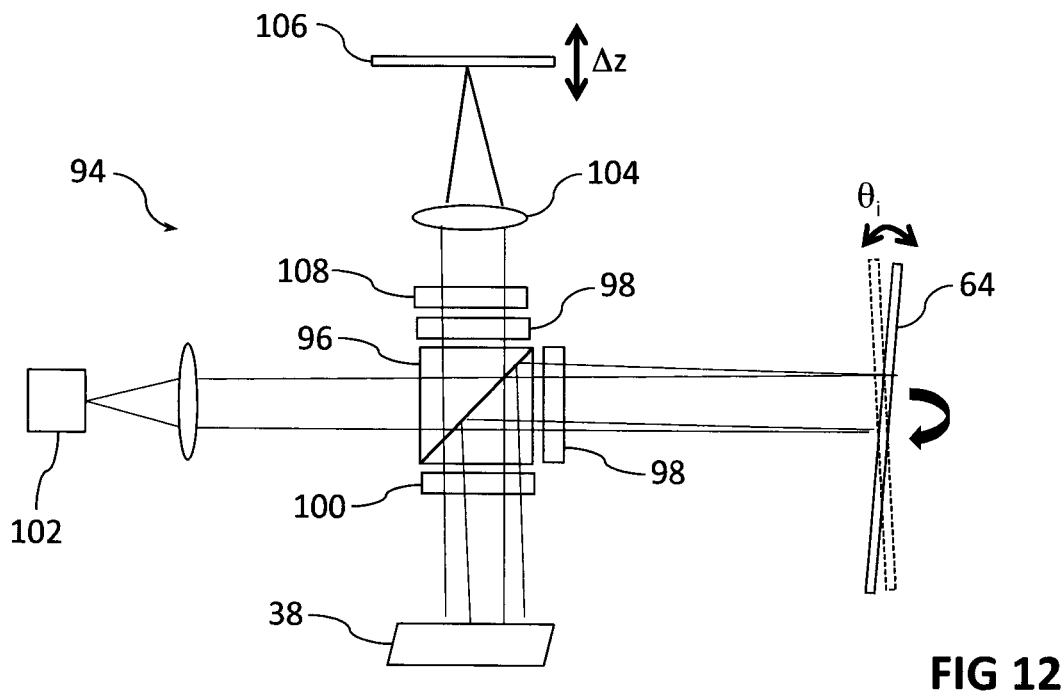
FIG. 12 illustrates an apparatus for analysing wavefronts based on a polarisation Twyman-Green interferometer.

An experimental demonstration of the core features of a single wavelength embodiment, such as that shown in FIG. 3, is described with respect to the simplified apparatus shown in FIG. 12. This apparatus uses a polarisation Twyman-Green interferometer 94 to generate and combine reference and sample beams via a polarisation beam splitter 96, quarter waveplates 98 and a polarisation analyser 100. In this case, for ease of demonstration, the light source is a continuous wave (CW) broadband source 102 filtered to reduce the bandwidth. In this context we note that some degree of bandwidth is useful for reducing the effects of spurious reflections and speckle, while too much bandwidth leads to a lack of coherence contrast across the photodetector array 38. Fringe patterns are measured with a photodetector array for a range of discrete reference beam angles $\theta_i$ selected by a scanning mirror 64 scanned in one or two axes. In this particular example the photodetector array 38 is a 2048×2752 pixel CCD camera with a pixel size of 4.54 μm. The reference beam has a full width half maximum diameter of 3.9 mm and the wavefront is calculated over a circular area of diameter corresponding to 1024 pixels on the photodetector array 38. The sample arm contains a f=30 mm achromatic doublet lens 104 and a mirror 106 positioned at a variable offset Δz with respect to the focal point of the lens 104 to induce defocus aberrations. The sample arm also contains an attenuator 108 set to emulate an appropriate sample reflectivity, e.g. −45 dB. It will be appreciated that a conventional power beam splitter could be used in the apparatus of FIG. 12, in place of the polarisation beam splitter 96, quarter waveplates 98 and analyser 100.

The defocus sample mirror 106 produces an expected aberration of $$D = \left(\frac{1}{f} - \frac{1}{f + 2\Delta z}\right),$$

which for f=30 mm and Δz=1 mm gives 2.1 diopters for example. Alternatively we can express the expected aberration in terms of the primary defocus Zernike coefficient using $$a_2^0 = \frac{\sqrt{3} D r_0^2}{12}$$

where $r_o$ is the radius over which the reflected wavefront is measured. We note that aberrations in the peripheral field angles of ±60 degrees of up to ±10 diopters have been observed in some individuals.

A number of interferograms were measured for different levels of defocus, each measurement having a different reference beam angle and a sampling time of 500 μs. The interferograms were then summed to emulate a pulsed source with scanning reference and sample mirrors as used in the apparatus of FIG. 3 for example. The combined interferograms were then subjected to the 2D FFT analysis described above with respect to FIG. 2 to yield a two dimensional map of the phase for each individual carrier, i.e. for each level of defocus.

Figure 13A:
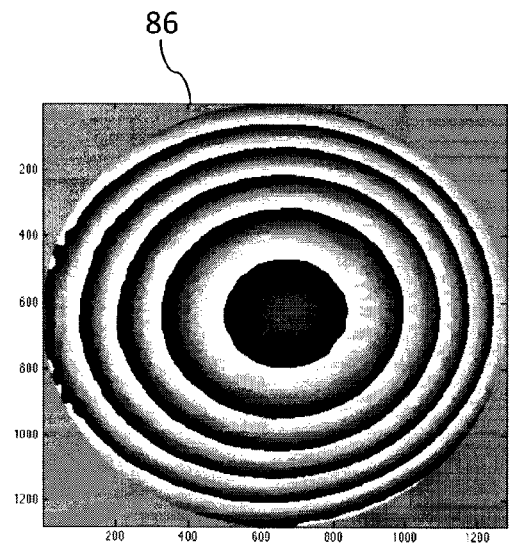
FIGS. 13a and 13b show the wrapped and unwrapped phase for a wavefront with 0.5 mm defocus measured with the apparatus of FIG. 12.
Figure 13B:
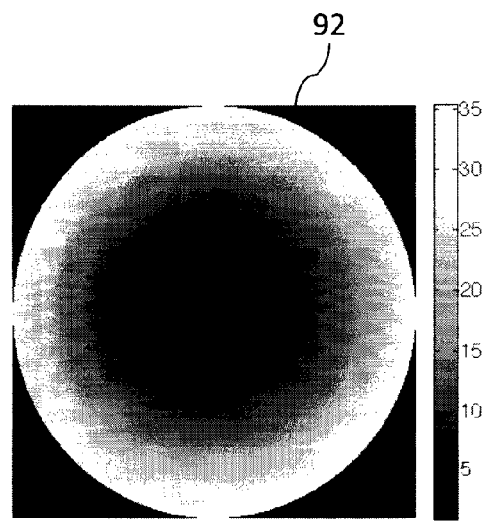
Figure 14:
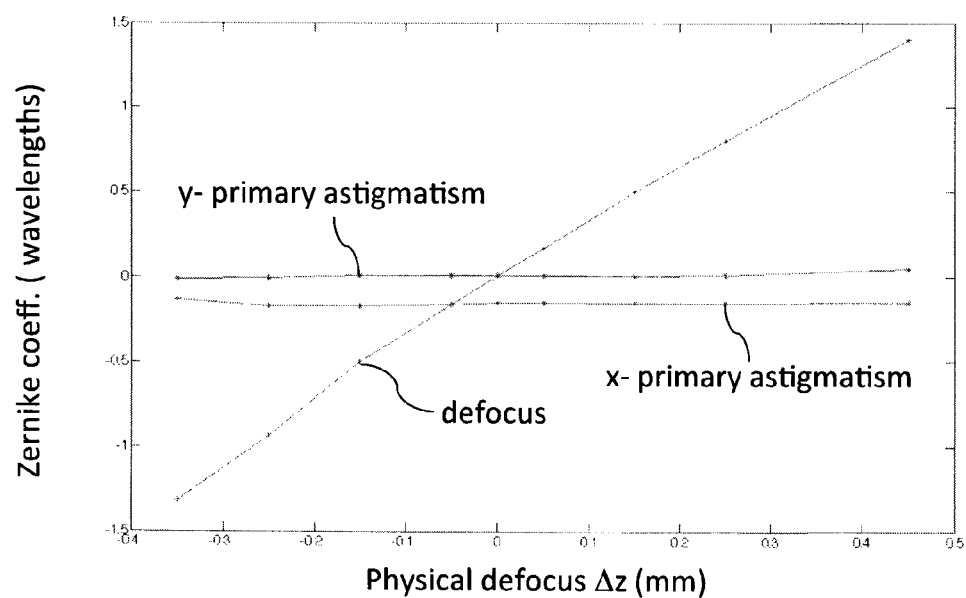
FIG. 14 shows a plot of calculated Zernicke coefficients for primary defocus and x- and y-primary astigmatism versus physical defocus Δz in the apparatus of FIG. 12.

FIG. 13a shows the wrapped phase 86 obtained from Fourier Transform analysis of a wavefront measured with the apparatus of FIG. 12, with Δz=0.45 mm defocus at the mirror 106, corresponding to D=0.97 diopters. The unwrapped phase 92 shown in FIG. 13b was then obtained using a branch cut phase unwrapping algorithm. The wavefront at the achromatic lens 104 can be determined by back propagating the measured wavefront from the CCD 38 to the lens, although in practice the provision of relay optics between the lens 104 and the CCD 38 would remove the need for this mathematical back propagation. The Zernike coefficients are then obtained by integrating the product of the wavefront and associated Zernike polynomials; for this particular wavefront we obtained $a_2^0$=1.40, $a_2^1$=0.05 and $a_2^{-1}$−0.15. Sample results for Zernike coefficients for primary defocus and primary astigmatism versus the physical defocus Δz are shown in FIG. 14. After back propagating the field at the detector 38 to the lens 104 a linear relationship between expected and measured primary defocus is obtained. The standard deviation of shot to shot measurements of the primary defocus was less than 1%, and the small levels of measured astigmatism are within expected levels for the experimental setup.

Wavefront Measurement with Simultaneous Optical Path Length Measurement

Figure 6:
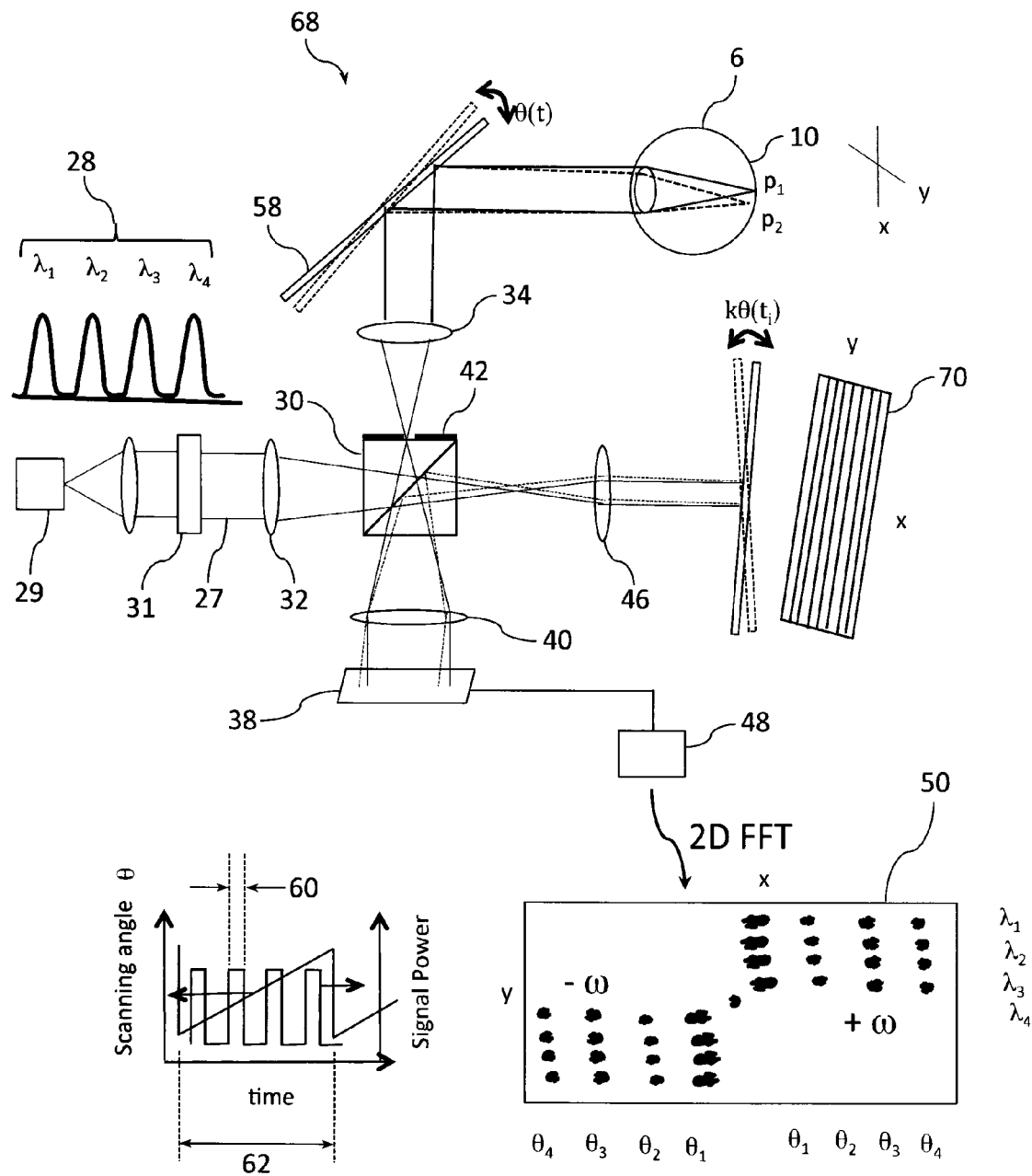
FIG. 6 illustrates an apparatus for analysing one or more wavefronts from an eye according to a third embodiment of the invention.

FIG. 6 illustrates an apparatus 68 according to a third embodiment of the invention, again based on a Twyman-Green interferometer, suitable for measuring simultaneously the aberrations of one or more sample wavefronts together with the associated optical path length in a sample such as an eye 6. Measurement of optical path length enables us for example to distinguish whether aberrations in the peripheral vision are due to changes in length of the eye under test 6 or to aberrations induced by the lens or cornea.

In this embodiment an incoming light field comprising a collimated beam 27 with multiple distinct narrow bandwidth components 28 is obtained from a broad wavelength low coherence optical source 29 filtered by an etalon 31. The narrow bandwidth components preferably have bandwidths in the range of 0.005 to 0.3 nm. A beam splitter 30 splits the incoming collimated beam 27 into a sample beam and a reference beam, with the sample beam directed by a 4F optical system comprising relay lenses 32 and 34 onto a scanning mirror 58 that deflects the sample beam onto the pupil of an eye under test 6 with a time varying field of view angle. As with the second embodiment shown in FIG. 3 for example it is convenient to use a pulsed light source 29 such as a pulsed laser with a pulse window time 60 that is substantially shorter than the mirror scan period 62. Preferably the pulse window time 60 is of order one hundred times shorter than the mirror scan period 62. More preferably the pulse window time 60 is of order one thousand times shorter than the mirror scan period 62. In this manner the eye can be sampled at a discrete set of view angles, with the eye focusing the sample beam onto a discrete set of spots $p_1$, $p_2$ etc on the retina 10. In this embodiment however each field of view angle contains multiple distinct wavelength components, e.g. four narrow band components $\lambda_1 \ldots \lambda_4$.

The light reflected from the retina 10 is subjected to aberrations from the eye and reflected by the scanning mirror 58 on its return path. The aberrated wavefronts are transmitted through the beam splitter 30 and projected onto a photodetector array 38 via a 4F optical system comprising the lenses 34, 40 and optionally a circular aperture 42. The aperture, if present, is preferably circular, with size chosen so as to limit the maximum aberration measurable, thereby minimising crosstalk between sample wavefronts. The reciprocity of the system ensures that on their return paths the wavefronts of all pulses (from different visual field angles) are parallel to each other at the photodetector array 38.

Turning now to the reference arm of the Twyman-Green interferometer, the reference beam from the beam splitter 30 is incident on a scanning element in the form of a rotating reflective diffraction grating 70 that is scanned synchronously with respect to the scanning mirror 58 in the sample arm. Typically some form of computer control is used to ensure the synchronous scanning of the mirror 58 and the grating 70. The diffraction grating 70 is configured such that its grating axis is perpendicular to the direction in which it is scanned. The reflected reference wavefronts are projected onto an image capture device 38 via a 4F optical system comprising lenses 40, 46 and reflection at the beam splitter 30, with angle of incidence determined in a first axis by the angle of the rotating grating $k\theta(t_i)$ associated with the pulse time $t_i$ of the incoming collimated beam 27, and in a second axis by the component wavelength.

As in the embodiment described above with respect to FIG. 3 the sample wavefronts reflected from the sequence of spots $p_n$ on the retina 10 mix with the reflected reference fields to produce a rapid sequence of interferograms or fringe patterns, each with a well-defined spatial period determined by the angle between the respective sample and reference wavefronts. The interferograms are produced on the photodetector array 38 in a time period determined by the scan period, e.g. 50 ms, which is chosen to be sufficiently short so as to enable 'single shot' capture, i.e. acquisition in a single exposure of the photodetector array. As in previously described embodiments each individual interferogram is preferably captured by the photodetector array in around 1 ms or less to avoid phase wash out. FIG. 6 includes a schematic 50 of the magnitude of the 2D-FFT of the composite interferogram, showing distinct carrier components for the distinct field of view angles at the eye ($\theta_1 \ldots \theta_4$ in this case) and for the different wavelength components ($\lambda_1 \ldots \lambda_4$ in this case). The wavefront for each carrier component is determined as described above in relation to FIG. 2. For each field of view, or spot on the retina 10, there are now several wavelength components with distinct spatial carrier frequencies. Averaging over the associated wavelength components may increase the accuracy of the measured aberration for a given field of view angle. In addition, it is well known in the field of fringe analysis that the robustness of phase unwrapping algorithms can be improved by using data from multiple wavelengths.

In preferred embodiments, for a given field of view the relative phase between distinct wavelength components in the 2D-FFT 50 shown in FIG. 6 is used to infer optical path length, as is known from Linear Optical Coherence Tomography (OCT). For cases in which there is negligible dispersion, the summation of the spatial frequencies along the dispersive axis can create a correspondence between depth of a sample reflection point and the spatial interference envelope.

Figure 7:
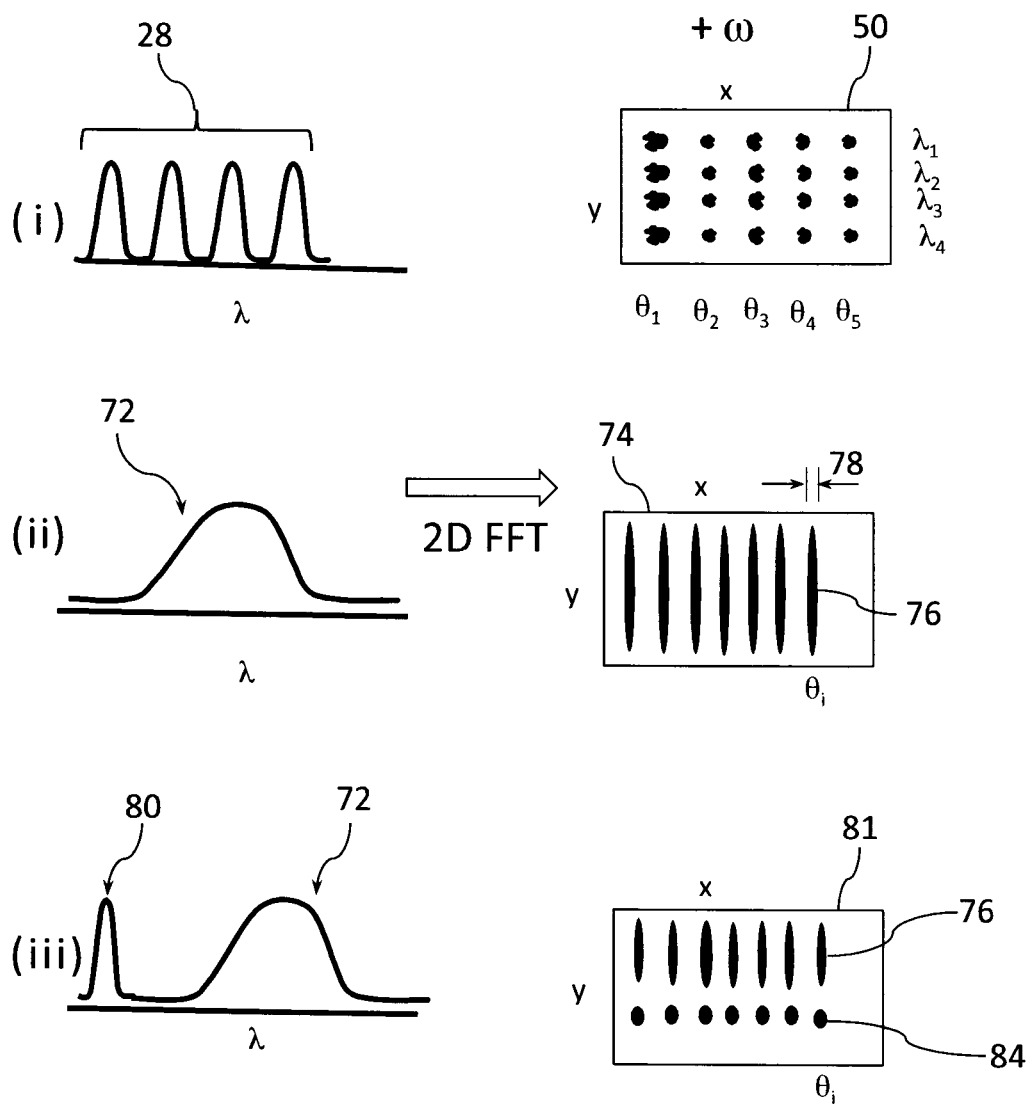
FIG. 7 shows a number of alternative wavelength distributions for an incoming beam, for simultaneous wavefront and optical path length measurements.

FIG. 7 shows a number of alternative wavelength distributions for an incoming beam, for simultaneous wavefront and optical path length measurements using the apparatus 68 of FIG. 6. Case (i), using a pulsed incoming beam with multiple distinct narrow wavelength band components 28, has been described in relation to FIG. 6. One alternative approach, case (ii), uses a pulsed beam with a broad wavelength distribution 72. In preferred embodiments the wavelength distribution 72 is 10 to 60 nm in width. When used in the FIG. 6 apparatus this results in a 2D FFT 74 that, unlike the corresponding 2D FFT 50 for case (i), no longer has distinct spatial carriers for the wavelength components. Optical path length for the $i^{th}$ point on the retina can be calculated from the $i^{th}$ frequency component 76 of the 2D FFT 74 using known Linear Domain OCT techniques, but the continuous distribution of wavelengths makes it difficult to determine the aberrations along the direction in which the wavelength components are spread. We are, however, able to determine the primary defocus along the perpendicular axis for the $i^{th}$ point on the retina from the width 78 of the $i^{th}$ frequency component 76 of the 2D FFT 74. A full two dimensional wavefront could alternatively be measured with a second scan without dispersion, for example by rotating the reference arm diffraction grating 70 such that the reflection from the zero order mode is incident upon the photodetector array 38.

A second alternative approach, case (iii), uses a pulsed beam having a narrow wavelength component 80 and a broad wavelength component 72, produced for example by multiplexing a narrowband source and a broadband source. Preferably the bandwidths of the narrow and broad wavelength components are in the range of 0.005 to 0.3 nm and 10 to 60 nm respectively. In one specific example the narrow and broad wavelength components have bandwidths of 0.05 nm and 30 nm respectively. When used in the FIG. 6 apparatus this type of wavelength distribution results in a 2D FFT 81 with a distributed frequency component 76 (associated with interference of the broad wavelength component) and a discrete frequency component 84 (associated with interference of the narrow wavelength component) for each spot on the retina. In this case the optical path length for each spot can be calculated from the distributed frequency component 76 using Linear OCT techniques, and the wavefront for each spot calculated from the discrete frequency component 84 using the above described inverse-FFT and phase unwrapping techniques. We note that it is possible in the mathematical analysis to correct for the wavefront distortion in the distributed frequency component, prior to determining path length difference.

Scanning System

We turn now to discussion of preferred systems for scanning the sample beam, in particular for ocular examination where it is preferable to be able to measure a wavefront of approximately 5 mm diameter over a large field of view (e.g. ±45 degrees) at the eye. With reference to FIGS. 3 to 6, the sample arm scanning mirror 58 is preferably in the form of a MEMS (micro-electro-mechanical) mirror, which has the advantages of low cost, light weight and fast response time. However MEMS mirrors generally have limited rotation angles (±3 degrees) and small diameters (2-3 mm). A key aspect of the present invention is the use of a telescopic lens system including a micro lens array, which enables a MEMS mirror of limited size and range of rotation (±3 degrees) to be scanned over a large field of view in discrete steps.

Figure 15:
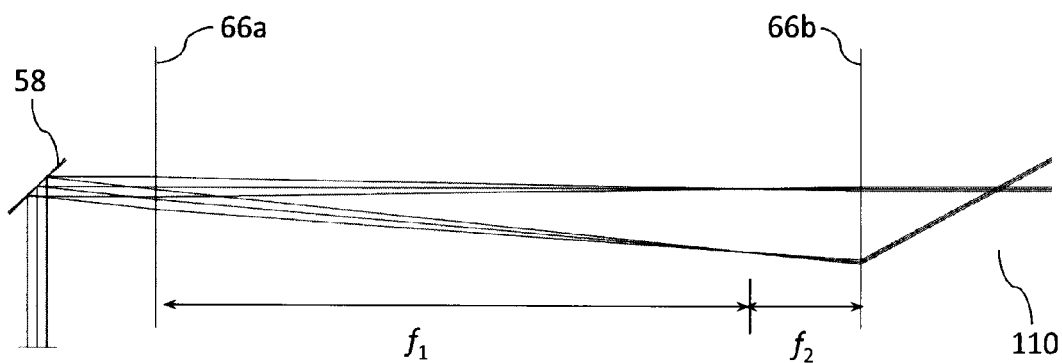
FIG. 15 shows a telescopic relay system for magnifying the range of viewing angles achievable with a scanning mirror of limited rotation angle range.

As mentioned above with regard to FIG. 5, the provision of a pair of relay lenses 66a, 66b in a telescope configuration allows tuning of the range of angles provided by a scanning mirror 58. In particular, and as illustrated in FIG. 15, it is known that a telescopic relay system comprising a short focal length lens 66b close to the pupil position 110 and a long focal length lens 66a towards the scanning mirror 58 will magnify small scanning mirror angles to large angles into and out of the pupil. If we define the focal lengths of the long focal length lens 66a and the short focal length lens 66b to be $f_1$ and $f_2$ respectively, the magnification of the scanning angle of a scanning mirror 58 is equal to twice the ratio of the focal lengths $2f_1/f_2$. However this system will also magnify the diameter of the wavefront reflected from the eye by a factor of $f_1/f_2$. For example if $f_1/f_2=4$ a wavefront with diameter 5 mm as it exits the pupil will be magnified to a diameter of 20 mm at the scanning mirror 58, which is much larger than the diameter of a typical MEMS-style mirror (2-3 mm).

Figure 16:
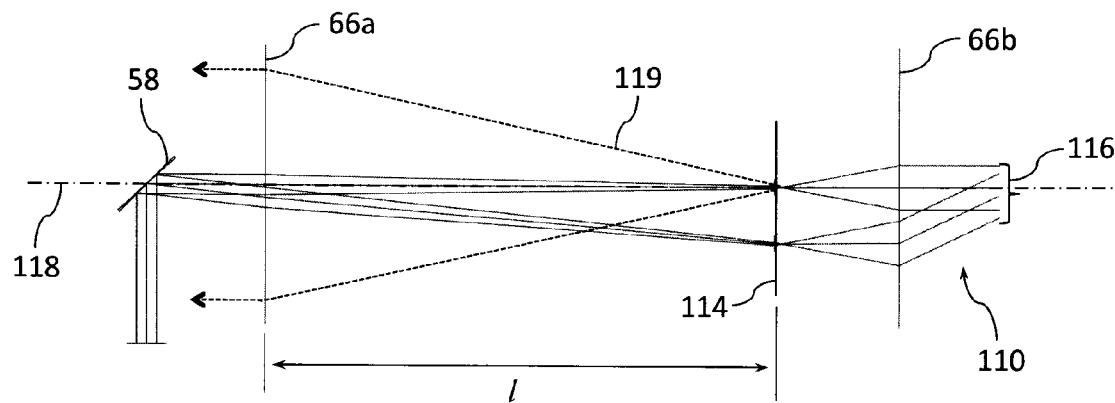
FIG. 16 illustrates how the telescopic relay system of FIG. 15 can be improved by the addition of a micro lens array.

To overcome this problem a micro lens array is used to perform a numerical aperture (NA) conversion within the telescopic system. As illustrated in FIG. 16, a micro lens array 114 of focal length $f_{MLA}$ and lens pitch d is placed close to the focal point of the lens 66b, with l defined to be the distance between the lens 66a and the micro lens array 114. The focal plane of the lens 66a and the micro lens array 114 in combination is aligned with the focal plane of the lens 66b. If we define the beam diameters at the pupil position 110 and at the scanning mirror position to be $w_1$ and $w_2$ respectively the ratio of beam sizes reduces to $w_1/w_2 = F_1/f_2$ where $$F_1 = \frac{f_1 f_{MLA}}{f_1 + f_{MLA} - l}$$

is the effective focal length of the combined lens 66a and the micro lens array 114. The step size between the discrete visual field angles at the pupil position 110 is given by $\Delta\theta = d/f_2$ radians, and the micro lens array may for example have fifty lenslets in a linear array.

By way of specific example, we consider a sample wavefront 116 at visual field angle of 30 degrees as shown in FIG. 16. At the pupil position 110 this wavefront has a diameter of 5 mm and an angle with respect to the optical axis 118 of 30 degrees. The wavefront passes through a collimating lens 66b of focal length $f_2=30$ mm and a diameter of 45 mm, and is focused at the image plane of the combined lens 66a and micro lens array 114. The lenslets in the micro lens array are on a pitch of d=500 μm and have a focal length of $f_{MLA}=1.4$ mm. The micro lens array 114 is placed a distance l=137 mm from the lens 66a, which has a focal length of $f_1=150$ mm, and 30.9 mm from the lens 66b. The effective focal length of the combined lens is F=14.6 mm, giving $w_1/w_2=\frac{1}{2}$. The micro lens array 114 has therefore decreased the beam diameter such that it is now only 2.5 mm in diameter at the long focal length lens 66a, and therefore at the scanning mirror 58, which is suitable for a MEMS-style mirror. Importantly, the beam angle with respect to the optical axis 118 is reduced from 30 degrees at the pupil to 6 degrees at the scanning mirror, which corresponds to a ±3 degree rotation in the scanning mirror and is likewise suitable for a MEMS-style mirror. By way of comparison the beam size that would eventuate in the absence of the micro lens array 114 is indicated by the rays 119.

As described previously the diameter of the sample beam incident on the eye is preferably small, for example 1 mm, to minimise the influence of aberrations on the path into the eye. In this case the introduction of the micro lens array 114 requires the incident beam to have a diameter of 0.5 mm at the scanning mirror 58.

In embodiments containing a scanning mirror 64 in the reference arm, this scanning mirror is likewise preferably a MEMS-style mirror. The reference arm is well suited for this sort of mirror because the required angular scanning range is typically only a few degrees.

With reference to FIG. 2, a telescopic lens system such as that shown in FIG. 15 is also useful for magnifying the wavelength dispersion provided for example by the sample arm diffraction grating 36. Typical diffraction gratings can provide angular dispersions in the range of around ±3 degrees, similar to the rotation range of a MEMS mirror. A micro lens array can likewise be used to control the diameter of the returning sample wavefront, although this is somewhat less critical since diffraction gratings are generally larger in extent than MEMS mirrors.

It will be appreciated that the illustrated embodiments enable the rapid analysis of one or more wavefronts obtained from a sample, via the formation and analysis of two or more interferograms with unique carrier frequencies. Multiple interferograms can be formed from one or more sample wavefronts by mixing them with multiple reference wavefronts, with the carrier frequencies determined by the angles between the sample wavefront and each reference wavefront. This is a particularly simple means for producing multiple spatial carriers for multiplexing wavefront measurements. The unique carrier frequencies are determined by the respective angles between sample and reference wavefronts. In preferred embodiments the sample wavefronts are propagating in parallel so that the respective angles are determined by the propagation directions of the multiple reference wavefronts.

In preferred embodiments the interferograms are formed with a Twyman-Green interferometer, which offers the benefit of interferometric gain associated with mixing a weak sample wavefront with a much stronger reference wavefront. This is particularly advantageous for ocular examination where the wavefronts reflected from the retina of an eye under test are extremely weak. This is to be contrasted with shearing interferometry where measurements are reliant on the interference of two copies of a sample signal, although shearing interferometry is somewhat less prone to motion artefacts. Further advantages with our techniques are direct measurement of phase as opposed to gradient of phase, which may be less prone to mathematical propagation of errors when determining phase, and compatibility with Linear OCT techniques for simultaneous measurement of wavefront aberration and optical path length.

In preferred embodiments the interferometer portion of the wavefront analyser is configured such that the two or more reference wavefronts are collimated when they interfere with the one or more sample wavefronts, since this simplifies the fringe pattern analysis. This is not a strict requirement so long as the reference wavefronts can be calibrated independently. It is also possible to calibrate a given wavefront analyser apparatus, including the sample arm, to remove instrument-induced aberration.

The methods and apparatus of the present invention have been described with reference to reflective samples, in particular eyes. However it will be appreciated by those skilled in the art that the methods and apparatus could also be applied with minor modifications to transmissive samples, e.g. using a Mach-Zehnder interferometer instead of a Twyman-Green interferometer.

Although the invention has been described with reference to specific examples, it will be appreciated by those skilled in the art that the invention may be embodied in many other forms.

The invention claimed is:

1. An apparatus for analysing one or more wavefronts from a sample, said apparatus comprising an interferometer and an image capture device, said interferometer being adapted to:
    split an incoming light field into a sample beam and a reference beam, thereby defining a sample arm and a reference arm;
    direct said sample beam onto a sample to form one or more wavefronts from said sample;
    separate said reference beam into two or more reference wavefronts; and
    mix said one or more sample wavefronts with said two or more reference wavefronts to form two or more interferograms on said image capture device for capture in a single exposure of said image capture device, wherein each interferogram has a discrete carrier frequency dependent on a respective angle between a sample wavefront and a reference wavefront.

2. An apparatus according to claim 1, wherein said incoming light field comprises two or more distinct wavelength components, and said reference arm comprises a first wavelength dispersive element for separating said reference beam into said two or more reference wavefronts on the basis of said wavelength components.

3. An apparatus according to claim 2, wherein said sample arm comprises a second wavelength dispersive element for directing said sample beam onto two or more regions of said sample on the basis of said wavelength components, to form two or more sample wavefronts.

4. An apparatus according to claim 2, wherein said first wavelength dispersive element is adapted to scan said reference beam in the direction normal to its dispersive axis, to provide a two dimensional grid of carriers in the frequency domain.

5. An apparatus according to claim 4, wherein said incoming light field is provided by a pulsed light source having a pulse window time that is substantially shorter than a period with which said reference beam is scanned.

6. An apparatus according to claim 2, wherein said reference arm comprises a scanning mirror adapted to scan said reference beam in the direction normal to the dispersive axis of said first wavelength dispersive element, to provide a two dimensional grid of carriers in the frequency domain.

7. An apparatus according to claim 6, wherein said incoming light field is provided by a pulsed light source having a pulse window time that is substantially shorter than a period with which said reference beam is scanned.

8. An apparatus according to claim 2, wherein said sample arm comprises a first scanning element for directing said sample beam onto two or more regions of said sample in sequence, and said first wavelength dispersive element is adapted to scan said reference beam in the direction normal to its dispersive axis, synchronously with respect to said first scanning element, to provide a two dimensional grid of carriers in the frequency domain.

9. An apparatus according to claim 8, wherein said incoming light field is provided by a pulsed light source having a pulse window time that is substantially shorter than a scan period of said first scanning element, or substantially shorter than a period with which said reference beam is scanned.

10. An apparatus according to claim 1, wherein said reference arm comprises a second scanning element adapted to be scanned in one or two axes, for separating said reference beam into said two or more reference wavefronts, and said sample arm comprises a first scanning element adapted to be scanned in one or two axes for directing said sample beam onto two or more regions of said sample to form two or more sample wavefronts, wherein the scanning of said first and second scanning elements is synchronous in at least one axis.

11. An apparatus according to claim 10, wherein said incoming light field is provided by a pulsed light source having a pulse window time that is substantially shorter than a scan period of said first or second scanning element.

12. An apparatus according to claim 1, wherein said interferometer comprises a non-polarising splitter for splitting said incoming light field into said sample and reference beams, and said reference arm comprises polarisation dispersive optics for separating said reference beam into said two or more reference wavefronts.

13. An article of manufacture comprising a non-transitory computer usable medium having a computer readable program code configured to operate the apparatus according to claim 1.

14. A method for analysing one or more wavefronts from a sample, said method comprising the steps of:
    splitting an incoming light field into a sample beam and a reference beam;
    directing said sample beam onto a sample to form one or more wavefronts from said sample;
    separating said reference beam into two or more reference wavefronts;
    mixing said one or more sample wavefronts with said two or more reference wavefronts to form two or more interferograms on an image capture device in a sufficiently short time period for said image capture device to capture said interferograms in a single exposure, wherein each interferogram has a unique carrier frequency dependent on a respective angle between a sample wavefront and a reference wavefront;
    capturing said two or more interferograms in a single exposure of said image capture device; and processing said two or more interferograms to extract phase information from each of said one or more sample wavefronts.

15. A method according to claim 14, wherein said incoming light field comprises two or more distinct wavelength components, and said reference beam is separated into said two or more reference wavefronts using a first wavelength dispersive element.

16. A method according to claim 15, wherein said sample beam is directed onto two or more regions of said sample using a second wavelength dispersive element, to form two or more sample wavefronts.

17. A method according to claim 15, wherein said first wavelength dispersive element scans said reference beam in the direction normal to its dispersive axis, to provide a two dimensional grid of carriers in the frequency domain.

18. A method according to claim 15, wherein a scanning mirror scans said reference beam in the direction normal to the dispersive axis of said first wavelength dispersive element, to provide a two dimensional grid of carriers in the frequency domain.

19. A method according to claim 15, wherein said sample beam is directed onto two or more regions of said sample in sequence using a first scanning element, and said first wavelength dispersive element scans said reference beam in the direction normal to its dispersive axis, synchronously with respect to said first scanning element, to provide a two dimensional grid of carriers in the frequency domain.

20. A method according to claim 14, wherein said reference beam is separated into said two or more reference wavefronts using a second scanning element scanned in one or two axes, and said sample beam is directed onto two or more regions of said sample, to form two or more wavefronts, using a first scanning element scanned in one or two axes, wherein the scanning of said first and second scanning elements is synchronous in at least one axis.

21. A method according to claim 14, wherein said splitting step is performed using a non-polarising splitter, and said reference beam is separated into said two or more reference wavefronts using polarisation dispersive optics.

22. An article of manufacture comprising a non-transitory computer usable medium having a computer readable program code configured to implement the method according to claim 14.

23. An apparatus for analysing one or more wavefronts from a sample, said apparatus comprising an interferometer and an image capture device, said interferometer being adapted to:
split an incoming light field into a sample beam and a reference beam, thereby defining a sample arm and a reference arm;
direct said sample beam onto a sample to form one or more wavefronts from said sample;
separate said reference beam into two or more reference wavefronts; and
mix said one or more sample wavefronts with said two or more reference wavefronts to form two or more interferograms on said image capture device, wherein each interferogram has a unique carrier frequency dependent on a respective angle between a sample wavefront and a reference wavefront, and wherein said interferometer is adapted to form said two or more interferograms in a sufficiently short time period for said image capture device to capture said interferograms in a single exposure, and wherein said interferometer comprises polarisation dispersive optics for determining a map of polarisation components across each of said one or more sample wavefronts.

* * * * *